United States Patent [19]

Gunther et al.

[11] Patent Number: 4,772,715

[45] Date of Patent: Sep. 20, 1988

[54] ISOTELLUROAZOLO[1,5-A]TEL-LURAZOLES AND PROCESSES FOR THEIR PREPARATION

[75] Inventors: Wolfgang H. H. Gunther, Webster; Rosemary Przyklek-Elling, Rochester, both of N.Y.

[73] Assignee: Eastman Kodak Company, Rochester, N.Y.

[21] Appl. No.: 892,553

[22] Filed: Aug. 4, 1986

Related U.S. Application Data

[63] Continuation-in-part of Ser. No. 702,695, Feb. 19, 1985, abandoned.

[51] Int. Cl.$^4$ ................ C07D 517/04; C07D 517/14; G03C 1/84
[52] U.S. Cl. .................................. 548/100; 430/510; 350/311
[58] Field of Search ........................................ 548/100

[56] References Cited

U.S. PATENT DOCUMENTS

| 2,168,174 | 8/1939 | Schlichting | 544/248 |
| 2,323,503 | 7/1943 | Wilson | 548/159 |
| 2,323,504 | 7/1943 | Wilson | 548/217 |
| 2,339,094 | 1/1944 | Middleton | 548/120 |
| 2,891,862 | 6/1959 | VanAllan | 548/120 X |
| 3,773,731 | 11/1973 | Ohi et al. | 548/120 X |
| 4,329,284 | 5/1982 | Detty et al. | 430/83 X |
| 4,365,016 | 12/1982 | Detty et al. | 430/83 |
| 4,365,017 | 12/1982 | Detty et al. | 430/83 |
| 4,575,483 | 3/1986 | Günther et al. | 430/588 |
| 4,576,905 | 3/1986 | Gunther et al. | 548/100 X |
| 4,578,348 | 3/1986 | Freeman et al. | 430/607 |
| 4,661,438 | 4/1987 | Przyklek-Elling et al. | 430/423 |

FOREIGN PATENT DOCUMENTS 0192466  8/1986  European Pat. Off. ............ 548/100
136420   of 0000 Japan .

OTHER PUBLICATIONS

T. H. James, The Theory of the Photographic Process, 4th Edition, Macmillan, 1977, pp. 205–212.
R. F. Hamer, Cyanine Dyes and Related Compounds, John Wiley & Sons, 1964, pp. 105, 106, and 117–120.
"Un Nouvel Heterocycle Tellure: le Benzisotellurazole-1,2", by Campsteyn et al., Journal of Heterocyclic Chemistry, vol. 15, Aug. 1978, pp. 745–748.
Perrier, et al., Chemical Abstracts, vol. 91, 56916z (1979).
Lucchesini, et al., Chemical Abstracts, vol. 100, 103251v (1984).

Primary Examiner—Donald G. Daus
Assistant Examiner—Diana G. Rivers
Attorney, Agent, or Firm—Carl O. Thomas

[57] ABSTRACT

Isotellurazolo[1,5-a]tellurazoles are disclosed. These heterocycles can be prepared by reacting a diarylformamidine with an aromatic tellurazolium salt which is substituted at its 2 ring position with a methine group precursor. The product heterocycles are useful directly for their blue light absorption and in forming stable heterocyclic nuclei containing compounds, such as a photographic addenda.

9 Claims, No Drawings

ISOTELLUROAZOLO[1,5-A]TELLURAZOLES AND PROCESSES FOR THEIR PREPARATION

This is a continuation-in-part of U.S. Ser. No. 702,695, filed Feb. 19, 1985, now abandoned.

FIELD OF THE INVENTION

This invention is directed to heterocycles containing nitrogen and tellurium atoms in a common ring. It relates especially to compounds containing three fused rings, including two fused rings containing tellurium and nitrogen and a third fused carbocyclic aromatic ring. The invention is also directed to a process for preparing and articles incorporating these heterocycles.

BACKGROUND OF THE INVENTION

Aromatic chalcogenazolium salts, such as benzoxazolium, naphthoxazolium, benzothiazolium, naphthothiazolium, benzoselenazolium, and naphthoselenazolium salts, as well as their azole, azoline, and azolinium derivatives, have been widely employed in silver halide photography. These compounds have been employed as nuclei in antifoggants or stabilizers, nucleating agents, latent image keeping addenda, and speed or contrast increasing addenda for silver halide photographic systems.

Aromatic chalcogenazolium salts are commonly incorporated as nuclei of polymethine dyes. A well known method for the synthesis of carbocyanine dyes employs 2-(2-acetanilidovinyl) substituted aromatic chalcogenazolium salts as intermediates, the latter being formed by reacting an N,N'-diarylformamidine with an aromatic chalcogenazolium salt substituted at its 2 ring position with a methine precursor, such as a methyl group, followed by treatment with a base and acetylation, either sequentially or concurrently. Carbocyanine dye synthesis can be completed by reacting the 2-(2-acetanilidovinyl) substituted aromatic chalcogenazolium salt with another azine or azole heterocycle also ring substituted with a methine group precursor, such as a 2-methyl substituted azole or 2- or 4-methyl substituted azine. Such carbocyanine dye syntheses are illustrated by T. H. James, *The Theory of the Photographic Process*, 4th Ed., Macmillan, 1977, pp. 205-212, and by F. M. Hamer, *Cyanine Dyes and Related Compounds*, John Wiley and Sons, 1964, pp. 105, 106, and 117-120.

Although Schlichting U.S. Pat. No. 2,168,174 and Wilson U.S. Pat. Nos. 2,323,503 and 504 have extended generic ring formulae to include tellurazoles as extrapolations of investigations of other chalcogenazoles, the true state of the art is summed up by Middleton, U.S. Pat. No. 2,339,094:

"It may be observed that the difficulty of reaction resulting in the production of azoles containing members of the oxygen group of elements in the azole ring may vary greatly with different elements, becoming greater in proceeding from the non-metallic elements such as oxygen and sulfur to the more strongly metallic elements such as selenium and tellurium. This probably accounts for the fact that many of the oxazoles and thiazoles have been known for years while the preparation of most of the selenazoles has been accomplished more recently and some of them are still unknown although the corresponding oxazoles and thiazoles are known. Furthermore, the tellurazoles from the simplest to the more complex derivatives have not been described up to the present time."

While the art has heretofore been unsuccessful in preparing tellurazolium salts and their derivatives, it should be noted that divalent tellurium atoms have been placed in other ring structures. Benzisotellurazole-1,2 is described in "Un Nouvel Heterocycle Tellure: le Benzisotellurazole-1,2", by Campsteyn et al, *Journal of Heterocyclic Chemistry*, Vol. 15, August 1978, pp. 745-748. Unfortunately no derivative of benzisotellurazole-1,2 is disclosed.

Tellurium atoms have been incorporated in ring structures other than azole or azine rings of various dyes. Japanese Kokai No. 136420, laid open Nov. 25, 1976, discloses a 1-tellura-3,5-cyclohexanedione nucleus in a merocyanine sensitizing dye in a silver halide emulsion. Detty et al U.S. Pat. No. 4,329,284 discloses 1,2-oxachalcogenol-1-ium salts, wherein the chalcogen can be tellurium or selenium, to be useful in photoconductive compositions. Detty et al U.S. Pat. Nos. 4,365,016 and 4,365,017 disclose tellurapyrylium dyes for use in photoconductive compositions.

In Gunther et al. U.S. Pat. No. 4,576,906 there are disclosed compounds containing an aromatic ring portion fused with a tellurazolium or derivative tellurazole, tellurazoline (including tellurazolinylidene), or tellurazolium ring portion together with processes and intermediates for their preparation.

SUMMARY OF THE INVENTION

In one aspect this invention is directed to a 1-arylisotellurazolo[1,5-a] aromatic tellurazole.

In another aspect this invention is directed to a material for filtering blue light comprised of a binder and a 1-arylisotellurazolo[1,5-a] aromatic tellurazole.

In an additional aspect this invention is directed to a filter for blue light comprised of a layer of this material.

In a further aspect this invention is directed to a photographic element comprised of a support and, coated on said support, a layer comprised of a 1-arylisotellurazolo[1,5-a] aromatic tellurazole.

In a still another aspect this invention is directed to a process of preparing a 1-arylisotellurazolo[1,5-a] aromatic tellurazole by preparing an aromatic tellurazolium heterocycle substituted at its 2 ring position with a methine group precursor and reacting the heterocycle with a diarylformamidine in the presence of a solvent.

DESCRIPTION OF PREFERRED EMBODIMENTS

To prepare a 1-arylisotellurazolo[1,5-a] aromatic tellurazole according to the present invention it is first necessary to prepare an aromatic tellurazolium salt which is substituted at its 2 ring position with a methine group precursor, such as methyl group. One such salt is a tellurium salt, such as illustrated by formula (I):

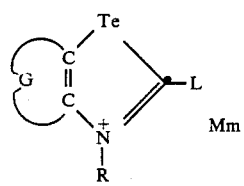

(I)

wherein

G represents the atoms completing a fused aromatic nucleus;

L represents a methine group precursor;

M represents a charge balancing counter ion;

m is 0 or 1; and

R is hydrogen or an optionally substituted hydrocarbon group.

It is by some procedures most convenient to prepare a tellurazolium salt according to formula (I) in the form in which R is hydrogen, hereinafter referred to as a protonated tellurazolium salt. The protonated tellurazolium salt can be deprotonated by treatment with a base to form the corresponding tellurazole. A quaternizing agent can be employed to convert the tellurazole to the corresponding tellurazolium salt containing an optionally substituted hydrocarbon group as the quaternizing substituent.

A first process for preparing a protonated tellurazolium salt satisfying formula (I) described above employs a starting material satisfying formula (II).

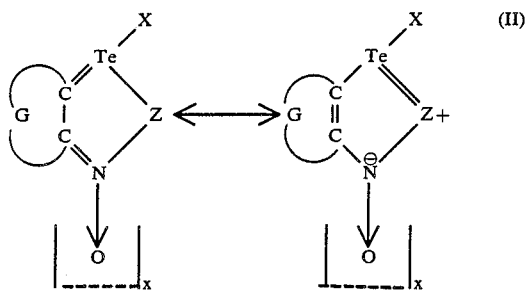

wherein
G represents the atoms completing a fused aromatic nucleus, x is zero or 1;

X is halogen or pseudohalogen;

Z is —O— or —N(R')—; and

R' is an aromatic nucleus.

When x is zero and Z is —N(R')—, the starting material can be (2-phenylazophenyl-C,N')tellurium(II) chloride, the preparation of which is described by Cobbledick et al, "Some New Organotellurium Compounds Derived from Azobenzene: The Crystal and Molecular Structure of (2-Phenylazophenyl-C,N')tellurium(II) Chloride", Journal of Chemical Research, pp. 1901–1924, 1979. Although Cobbledick et al employed chloride as the halogen corresponding to X in formula (II), it is apparent from the reported synthesis that X can be halogen (employed here and elsewhere to designate generically chloride, bromide, or iodide) or a pseudohalogen (i.e., one of the recognized class of substituents known to approximate the substituent properties of halogen), such as a cyano, thiocyanate, or hydroxy substituent. Similarly, G and R' can be varied merely by substituting for one or both of the phenyl groups employed in the phenylazophenyl employed by Cobbledick et al an alternative aromatic nucleus. In general the aromatic nuclei, which form G in each of its various occurrences and are referred to in other occurrences variously as aromatic rings, nuclei, or aryl groups or moieties, are preferably carbocyclic aromatic nuclei having from 6 to 20 carbon atoms, most preferably a phenyl or naphthyl or, in the fused form, a benzo or naphtho, nucleus. In some instances an aromatic nucleus can be fused through a five-membered ring, as is illustrated by acenaphthylene fused at its 1,2 ring edge. Since R' has little influence on the reaction and is not incorporated in the final product, R' can take a particularly wide variety of aromatic forms, but is generally most conveniently chosen from among the preferred forms of carbocyclic aromatic nuclei.

In an alternative form the first process can employ a starting material according to formula (II) in which x is zero and Z is oxygen. This compound can be formed by placing in solution an optionally substituted α-tetralone, hydrochloric or hydrobromic acid, tellurium dioxide, and hydroxylamine. This reaction has the advantage that all of the required materials are readily available at relatively low cost. Alcohols are convenient solvents for the reaction, although other nonreactive organic solvents can be employed. Heating is not required, but can accelerate the reaction. The material of formula (II) forms a solid phase which can be separated by routine filtering and washing steps. Both unsubstituted α-tetralone and various substituted derivatives are useful. Preferred α-tetralones can be represented by the formula:

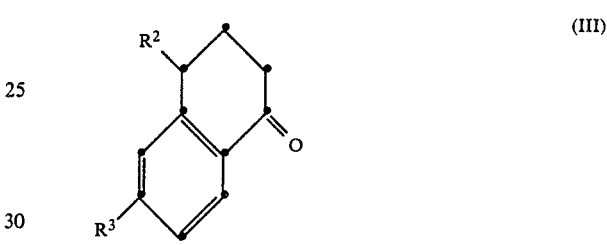

wherein $R^2$ and $R^3$ are independently selected from among hydrogen, halogen, alkyl, and alkoxy. Since $R^2$ and $R^3$ are naphtho ring substituents in the tellurazolium salt ultimately produced, it is apparent that the number of carbon atoms in the alkyl and alkoxy substituents can be widely varied. Instead of employing an α-tetralone, as described above, it is possible to employ a substituted or unsubstituted acenaphthen-1-one.

In general alkyl substituents and moieties of the tellurazolium salts and their derivatives are limited only by physical considerations, such as solubility, mobility, and molecular bulk. Generally alkyl and other aliphatic moieties of the tellurazolium salts and their derivatives of this invention are contemplated to contain up to 18 or more carbon atoms. Since increasing molecular bulk, except as sometimes required to reduce mobility, is seldom desirable in photographic applications, the preferred aliphatic hydrocarbon moieties contain up to 6 carbon atoms, with the lower alkyls (i.e., methyl, ethyl, propyl, and butyl) being preferred. In general, references to cycloalkyl indicate groups having 4 to 10 carbon atoms in a ring, with 5 or 6 ring carbon atoms being preferred.

Instead of preparing the starting material of formula (II) wherein x is zero and Z is oxygen in the manner described above, an oxime of an α-tetralone or acenaphthen-1-one described above can be reacted with tellurium tetrahalide, preferably tellurium tetrachloride or tellurium tetrabromide. In this and subsequent descriptions of employing tellurium tetrahalides as reactants it should be borne in mind that similar results can usually be obtained by reacting, before or during the α-tetralone or acenaphthen-1-one or reaction, a soluble halide salt, such as an alkali or alkaline earth halide, with tellurium dioxide. This is believed to generate a tellurium tetrahalide. A carboxylic acid can be employed as a solvent for the reaction, and the reaction can be accelerated by heating. The starting material of formula (II) forms a solid phase which can be separated by routine filtering and washing procedures. The preferred α-tetralone oximes correspond to the preferred α-tetralones and can be represented by the formula:

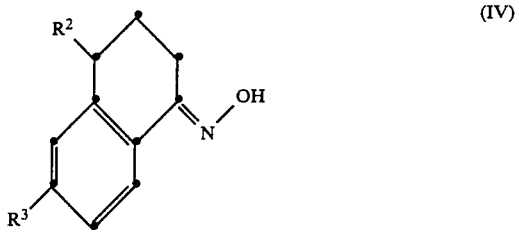
(IV)

wherein R² and R³ are chosen as described above.

In a third general form of the starting material of formula (II) x can be 1 and Z oxygen. This form of the starting material of formula (II) can be prepared by reacting with tellurium tetrahalide a carbocyclic aromatic compound activated for electrophilic substitution. Although naphthalene is illustrative of a fused ring carbocyclic aromatic compound that has been activated for electrophilic substitution, it is generally easiest to activate benzene. Activation can be achieved by employing electron donating substituents, such as hydroxy, hydroxyalkyl, alkyl, alkoxy, aryloxy, hydroxyaryl, amino, and groups of similar negative Hammett sigma values, singly or in combination. The reaction can be carrried out in an organic solvent such as a liquid hydrocarbon (e.g., benzene or cyclohexane), a halohydrocarbon (e.g., chlorobenzene or chloroform), a nitrohydrocarbon (e.g., nitromethane), or acetonitrile while heating to reflux. Formation of the starting material of formula (II) can be completed by nitrating and then treating with a reducing agent. Strong reducing agents can be employed in precisely stoichiometric concentrations or less. It is generally preferred to employ a mild or dilute reducing agent. Nitric acid in a suitable diluent, such as water or carboxylic acid, can be used for nitrating while hypophosphorous acid can be employed as the mild reducing agent. The synthetic route described above can be modified by a preliminary treatment with the mild reducing agent before nitrating and employing a strong nonoxidizing acid after nitrating and before employing the mild reducing agent a second time. In general the strong nonoxidizing acids contemplated for use in this and other steps of the preparation procedures herein described include acids such as hydrochloric acid, hydrobromic acid, sulfuric acid, fluoroboric acid, a sulfonic acid, and phosphoric acid.

A particularly preferred starting material prepared by the process described in the preceding paragraph can be represented by the formula:

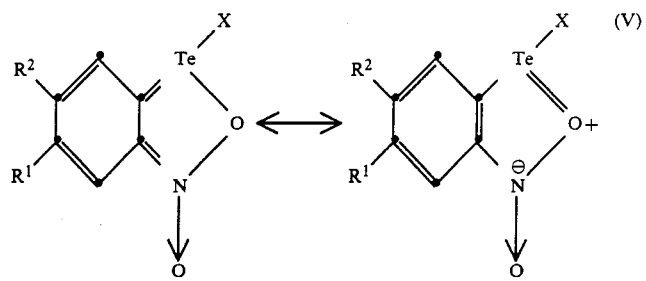
(V)

wherein at least one of R¹ and R² and preferably both are chosen from among hydroxy, hydroxyalkyl, alkyl, alkoxy, aryloxy, hydroxyaryl, and amino groups. Alternately R¹ and R² together can form an alkanediyldioxy linkage—e.g., a —O—(CH₂)ₙ—O— linkage, where n is preferably from 1 to 3. X is halogen or pseudohalogen, as previously described.

Once the starting material of formula (II) has been prepared, regardless of the choice of alternative preparation routes described above, it is treated with a strong alkaline reducing agent, such as an alkali borohydride (e.g., lithium, sodium, or potassium borohydride). The reaction product is then acylated with a compound according to formula (VI).

(VI)

wherein

L represents a methine group precursor and

Y is halogen or L—C(O)—O—.

From the value of Y, it is apparent that the acylating agent can be either acyl halide, such as acetyl chloride or acetyl bromide, or an acid anhydride, such as acetic anhydride. By noting the appearance of L in formulas (I) and (VI) it is also apparent that the acyl halide or acid anhydride also provides the 2-position substituent in the protonated tellurazolium salt. The L group serves the important purpose of providing a methine group forming the isotellurazole ring in the heterocycle ultimately produced. Generally this function is adequately served when L is a methyl group, but L can take the form of any methine group precursor desired. Producing the protonated tellurazolium salt is completed by treatment with a strong nonoxidizing acid, such as any of those mentioned above.

Another process for preparing a protonated tellurazolium salt according to formula (I) comprises employing a starting material according to formula (VII):

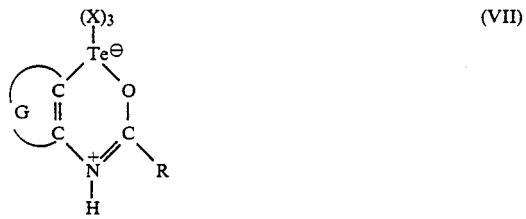
(VII)

wherein

G represents the atoms completing a fused aromatic nucleus;

L represents a methine group precursor; and

X represents halogen or pseudohalogen.

In formula (VII) the halogen or pseudohalogen represented by X and the methine precursor group represented by L can take any of the forms previously described. The starting material is reacted with a strong alkaline reducing agent, such as described above, and the resulting product is reacted with a strong nonoxidizing acid, such as also described above, to produce the desired protonated tellurazolium salt.

The starting material of formula (VII) can be prepared starting with a compound according to formula (VIII):

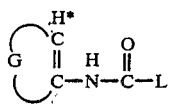
(VIII)

wherein:

H* is an activated hydrogen atom;

G represents the atoms completing an aromatic nucleus; and

L is a methine group precursor.

When the compound of formula (VI) is melted or heated in a suitable solvent (e.g., acetonitrile, butyronitrile, or chloroform) with tellurium tetrachloride or tellurium tetrabromide, the material of formula (VIII) is produced. Heating to a temperature of at least 60° C. up to about 140° C. is contemplated, with temperatures of from about 110° to 120° C. being preferred. If desired, the chloride or bromide in the formula (VII) compound can be displaced by iodide or pseudohalogen by treatment with iodide or pseudohalogen salt, thereby permitting the full range of values of X in formula (VII) to be realized. In part the reaction to produce the material of formula (VII) is accomplished by choosing G in formula (VIII) so that the aromatic nucleus which it completes is activated in the position ortho to the amido substituent. This can be accomplished by including in the aromatic nucleus one or more substituents capable of directing ring substitution in formula (VI) to the ring position of the starred activated hydrogen atom. For carbocyclic aromatic rings, such as benzene and naphthene rings, useful substituents can be chosen from among aliphatic and aromatic groups comprised of hydrocarbon moieties (e.g., alkyl, aryl, alkaryl, or alkaryl) optionally linked through a divalent oxygen or sulfur atom (e.g., an alkoxy, aryloxy, alkaryloxy, alkaryloxy, alkylthio, arylthio, alkylthio, or alkarylthio group); an amino group, including primary, secondary and tertiary amines; an amido group (e.g., acetamido and butyramido); a sulfonamido group (e.g. an alkyl or arylsulfonamido group); a sulfamoyl group (e.g. an alkyl or arylsulfamoyl group); a ureido group (e.g., 1-ureido, 3-phenyl-1-ureido, and 3-methyl-1-ureido); hydroxy; or a —C(O)M group or —S(O)$_2$M group, wherein M is chosen to complete an acid, ester, thioester, or salt (e.g., —C(O)OH, —C(O)SCH$_3$, —C(O)OCH$_3$, —C(O)ONa, —S(O)$_2$OH, —S(O)$_2$OCH$_2$C$_6$H$_5$, or —S(O)$_2$OLi). The aromatic nucleus completed by G as well as L can progress unaltered from the compound of formula (VIII) to the protonated tellurazolium salt.

In formula (I), where R is hydrogen, m is 1 and M is an anion, and is usually the anion of the last acid employed in the process. However, it is apparent that conversion from one anion to another can be easily accomplished and that the anion of the protonated tellurazolium salts can be varied widely.

To obtain the tellurazole corresponding to the protonated tellurazolium salt prepared as described above treatment with a base, such as ammonium hydroxide, an alkali hydroxide, or an alkali carbonate or bicarbonate, can be undertaken. Procedures for performing the same operation on known chalcogenazolium salts are directly applicable. The tellurazole product obtained is generally indicated by formula (IX):

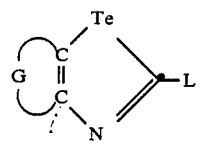
(IX)

wherein G and L correspond to their values in the parent protonated tellurazolium salt.

To convert the tellurazole of formula (IX) to a corresponding quaternized heterocyclic ammonium salt, the tellurazole is reacted with a quaternizing agent. Specifically preferred quaternizing agents are strong quaternizing agents, such as poly(fluoro)alkylsulfonic acid esters, such as aryl, alkenyl, alkynyl, aralkyl, or alkaryl esters of poly(fluoro)alkylsulfonic acid. Perfluorinated alkylsulfonic acid esters are particularly preferred quaternizing agents (e.g., trifluoromethylsulfonic acid esters). Arylsulfonic acid esters, such as para-toluenesulfonic acid esters, are also strong quaternizing agents. 1,3,2-Dioxathiane-2,2-dioxide and 1,3,2-dioxathiolane-2,2-dioxide have also been demonstrated to be useful quaternizing agents. Including electron donating ring substituents in the aromatic nuclei forming G in formula (IX) facilitates quaternization while strongly electron withdrawing substituents require strong quaternizing agents to be employed when quaternization occurs after tellurazole ring formation.

A very advantageous approach for preparing quaternized tellurazolium salts satisfying formula (I) is to employ a starting material according to formula (II) wherein x is zero. The starting material is first treated with a strong alkaline reducing agent, which can be selected from among those described above. The reaction product is then treated with an oxidizing agent, such as oxygen, a peroxide, a disulfide, or a sulfoxide, to produce

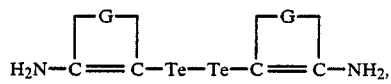
(X)

which is treated with an aldehyde, treated with a strong alkaline reducing agent, such as described above, and then treated with an acylating agent according to formula (VI), as described above, and a strong nonoxidizing acid, also as described above. Although treatment with an oxidizing agent is preferred, no separate oxidizing step is required. Ambient air will spontaneously perform such oxidation, and treatment with the aldehyde is sufficient in an inert atmosphere. A variety of quaternizing substituents can be introduced in the salt of formula (I) in addition to those provided by strong quaternizing agents, merely by appropriate selection of the aldehyde. Thus, in addition to hydrogen R in formula (I) can take the form of an optionally substituted hydrocarbon residue of an aldehyde quaternizing substituent, such as alkyl, alkenyl, alkynyl, or aralkyl moieties as well as substituted derivatives, such as oxy, thio, sulfo, sulfonyl, sulfato, halo, or carboxy substituted derivatives, often incorporated to modify solubility or other physical properties. Sulfoalkyl and sulfatoalkyl quaternizing substituents having from 1 to 6 carbon atoms are specifically preferred.

Once an aromatic tellurazolium salt is obtained a 1-arylisotellurazolo[1,5-a] aromatic tellurazole according to this invention can be prepared by reacting the 1-arylisotellurazolo[1,5-a] aromatic tellurazole with an N,N'-diarylformamidine in the presence of a solvent. Useful N,N'-diarylformamidines can be illustrated by formula (XI):

  (XI)

wherein
Ar¹ and Ar² are aromatic groups and
L² is a methine group.

The aromatic groups Ar¹ and Ar² are preferably carbocyclic aromatic groups, such as phenyl or naphthyl. The aromatic groups can be substituted, if desired. Such optional aromatic group substituents can be similar to the optional hydrocarbon group substituents described above in connection with R. The methine group is preferably —CH=, but the hydrogen can be replaced with a hydrocarbon group, if desired. For example, lower alkyl groups of from 1 to 6 carbon atoms are common pendant groups. When Ar¹ and Ar² are seen phenyl and L² is —CH=, the N,N'-diarylformamidine of formula (XI) is N,N'-diphenylformamidine, a preferred reactant.

As discussed above, when an aromatic chalcogenazole, differing from formula (I) in that an oxygen, sulfur, or selenium chalcogen atom is present in place of tellurium, is reacted with formamidine, the corresponding 2-(2-acetanilidovinyl) substituted compound is produced, which is a common intermediate in the preparation of cyanine and merocyanine dyes. Such reactions are performed using a variety of common organic solvents, such as alkanols (e.g., methanol, ethanol, propanol, isopropanol, n-butanol, tert-butanol, and the like); acetonitrile; aliphatic and aromatic hydrocarbons, such as toluene, xylene, and decane, as well as their halogenated analogoues; high boiling ethers; pyridine, dimethylsulfoxide; and dimethylformamide.

However, when an aromatic tellurazolium salt such as indicated by formula (I) is reacted with an N,N'-diarylformamidine in the types of solvents commonly employed to produce 2-(2-acetanilidovinyl) substituted aromatic chalcogenazoles, it is has been observed that the result is is not a b 2-(2-acetanilidovinyl) aromatic tellurazolium salt, but a 1-arylisotellurazolo[1,5-a] aromatic tellurazole, a novel heterocycle. Further, it is a heterocycle that has no known oxygen, sulfur, or selenium analogue. That is, no other isochalcogenazolo[1,5-a] aromatic chalcogenazole is known.

Formation of the 1-arylisotellurazolo[1,5-a] aromatic tellurazole occurs under the same conditions known to produce 2-(2-acetanilidovinyl) aromatic chalcogenazolium salts, such as 2-(2-acetanilidovinyl)benzoxazolium, 2-(2-acetanilidovinyl)benzothiazolium, and 2-(2-acetanilidovinyl)benzoselenazolium salts. The reaction generally takes place at room temperature, but can be accelerated by heating, if desired. If, instead of placing in a solvent, an aromatic tellurazolium salt such as indicated by formula (I) is melted with an N,N'-diarylformamidine and held at an elevated temperture, 2-(2-acetanilidovinyl) aromatic tellurazolium salt can be produced.

The preferred 1-arylisottellurazolo[1,5-a] aromatic tellurazoles according to this invention can be represented by formula (XII):

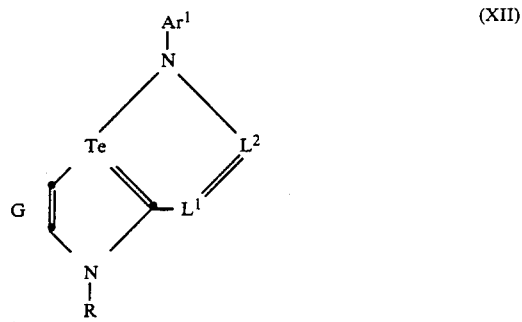

wherein
Ar¹ is an aromatic group;
G represents the atoms completing a fused aromatic nucleus;
L¹ and L² are methine groups; and
R is hydrogen or an optionally substituted hydrocarbon group.

Preferred selections of Ar¹, G, L¹, L², and R have been previously identified and discussed in connection with the starting materials, wherein corresponding moieties are represented by corresponding formula symbols.

Specifically preferred 1-arylisotellurazolo[1,5-a] aromatic tellurazoles according to this invention are 1-phenylisotellurazolo[1,5-a]benzotellurazoles, such as those represented by formula (XIII):

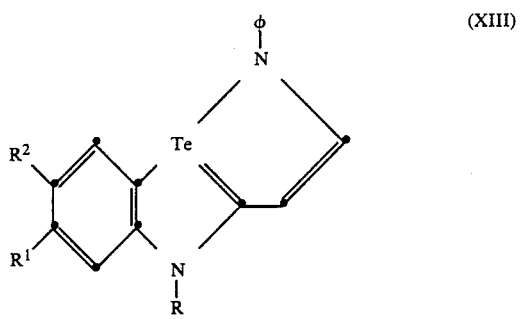

wherein
R is comprised of a hydrocarbon group selected from among alkyl, cycloalkyl, alkenyl, alkynyl, aryl, aralkyl, or alkaryl groups optionally substituted with one or more oxy, thio, sulfonyl, sulfato, halo, or carboxy groups;
R¹ and R² are individually chosen from among hydrogen, hydroxy, hydroxyalkyl, alkyl, alkoxy, alkylthio, aryloxy, arylthio, hydroxyalkyl, and amino groups or R¹ and R² together form an alkanediyldioxy linkage—e.g., a —O—(CH₂)ₙ—O— linkage, where n is preferably 1 to 3; and
φ represents a phenyl substituent.

In certain specific optimum forms, when R is alkyl, it can be chosen from among straight and branched chain alkyl groups having from 1 to 6 carbon atoms—e.g., methyl, ethyl, isopropyl, isobutyl, t-butyl, n-pentyl, neopentyl, and n-hexyl; when R is cycloalkyl, it can be chosen from cycloalkyl groups having from 3 to 8 carbon atoms—e.g., cyclopropyl, cyclopentyl, and cyclohexyl; when R is alkenyl, it can be chosen from among alkenyl groups having from 2 to 6 carbon atoms—e.g., vinyl, allyl, and 2,4-butadienyl; when R is alkynyl, it can chosen from alkynyl groups having from 2 to 6 carbon atoms—e.g., ethynyl, propargyl, and 3-butynyl; when R is aryl, it can be chosen from among aryl groups having from 6 to 10 carbon atoms—e.g., phenyl, 1-naphthyl, and 2-naphthyl; and when R is aralkyl or alkaryl, the alkyl and aryl moieties can be chosen from among the optimum alkyl and aryl substituents identied above. While the above optimum forms of R need not be further substituted, it is recognized that further substitution is possible. For example, one or more halo substituents of any one of the various forms of R are contemplated, where halo is selected from among fluoro, chloro, bromo, and iodo substituents; one or more carboxylate-forming substituents are contemplated, where the substituent is independently selected from among carboxylate-forming groups having from 1 to 8 carbon atoms—e.g., formyloxy, acetyloxy, and benzyloxy; oxyalkyl, oxyaryl, oxyalkaryl, oxyalkaryl, thioalky, thioaryl, thioalkaryl, and thioalkaryl groups are contemplated, where the alkyl and aryl moieties can take any of the various optimum forms previously described. Sulfonyl and sulfato substituents can be represented as —S(O$_2$)OM' and —OS(O$_2$)OM' substituents, respectively, where M' is hydrogen, ammonium ion, a metal cation—e.g., an alkali metal cation, or the atoms completing an ester—e.g., an alkyl or aryl group as above described.

In certain specific optimum forms of $R^1$ and $R^2$, where aryl or alkyl moieties are present, they can take any of the various optimum forms of these moieties described for R. When $R^1$ or $R^2$ is an amino group it can be an unsubstituted (i.e., primary) amine, a monosubstituted (i.e. secondary) amine, or a disubstituted (i.e., tertiary) amine, where the amine substituents can take any of the optimum forms of R described above, but are preferably alkyl or aryl substituents as above described in connection with R.

In one optimum form $\phi$ represents an unsubstituted phenyl group. However, in other optimum forms the phenyl substituent can be further substituted with any of the various groups described above as constituting optimum forms of R.

From the foregoing, it is apparent that in certain specifically preferred forms the compounds of formula (XIII) are chosen so that no one of the substituents R, $R^1$, and $R^2$ account for more than 10 carbon atoms.

One very specific grouping of the compounds of this invention is represented by formula (XIII) wherein R is chosen from the class consisting of alkyl benzyl, alkenyl, sulfoalkyl, and sulfatoalkyl, wherein each alkyl moiety contains from 1 to 6 (most preferably 1 to 3) carbon atoms;

$R^1$ and $R^2$ are chosen independently from the class consisting of hydrogen, alkyl, alkoxy, alkylthio, and phenoxy or together form a —O—(CH$_2$)$_n$—O— linkage, where n is preferably 1 to 3 and each alkyl moiety contains from 1 to 6 carbon atoms (most preferably from 1 to 3 carbon atoms); and $\phi$ is phenyl.

The isotellurazolo[1,5-a]tellurazole nucleus forms a blue absorbing chromophore. Thus, in the absence of other substituent chromophores, the 1-arylisotellurazolo[1,5-a] aromatic tellurazoles according to the present invention are bright yellow in appearance. The color and stability of the isotellurazolo[1,5-a]tellurazole nucleus allows the heterocycles of this invention to be employed to filter blue light.

The function of the aromatic nucleus G in formula (XII) is to facilitate synthesis of the tellurazole ring. Because of the further conjugation of double and single bonds which the aromatic nucleus brings to the compound, as is apparent from formula (XIII), it is conceivable that the aromatic nucleus could extend the wavelength of the dye chromophore further into the visible spectrum. However, any such bathochromic shift of light absorption would not be detrimental to the utility of the dyes of the invention as filter materials. Rather, such extension, if observed, can be readily applied to filtering light having wavelengths in spectral regions beyond the blue.

The nucleus substituents, such as possible substituents of the methine groups $L^1$ and $L^2$, $Ar^1$, $\phi$, R, $R^1$, and $R^2$ make no contribution to light absorption by the chromophore represented by the isotellurazolo[1,5-a]tellurazole nucleus. To the extent any substituent is chosen which itself contains a chromophore, the visual hue of the dye would be altered, but a separate chromophore would not prevent the isotellurazolo[1,5-a]tellurazole nucleus from absorbing blue light, although light of a different wavelength might also be absorbed by the separate substituent chromophore. Thus, so long as the isotellurazolo[1,5-a]tellurazole nucleus is present in the compounds of the invention filter dye utility is assured. The preferred nucleus substituents are dictated by synthetic convenience and have only secondary, if any, bearing of filter dye hue.

The 1-arylisotellurazolo[1,5-a] aromatic tellurazoles can be employed in either a solid crystalline or liquid form to filter light. Fabrication of filter layers, either as discrete elements or as components of elements, can be generally facilitated by dispersing the 1-arylisotellurazolo[1,5-a] aromatic tellurazoles in a binder or other dispersing vehicle.

In addition to their use in filtering blue light the 1-arylisotellurazolo[1,5-a] aromatic tellurazoles according to the present invention can be employed as alternatives to stable heterocyclic nuclei incorporated in a variety of compounds. Such nuclei are, for example, often employed to reduce mobility—e.g., as ballasts. Still other functions are possible.

The utility of 1-arylisotellurazolo[1,5-a] aromatic tellurazoles according to the present invention can be conveniently illustrated by reference to silver halide photography. In its most widely employed form silver halide photography employs for imaging radiation sensitive silver halide grains. The grains are suspended in a dispersing medium so that the grains and dispersing medium together form a radiation sensitive silver halide emulsion. The silver halide emulsions are typically coated on a photographic film or paper support to form a photographic element. A simple photographic element can consist of a support and an emulsion layer; however, typically additional layers, such as multiple emulsion layers, subbing layers, interlayers, and overcoats are also present. The silver halide emulsions can be usefully, though incompletely, categorized as those which form predominantly surface or predominantly internal latent images upon exposure. Photographic elements can be conveniently classified as being direct positive photographic elements or negative working photographic elements. Whether a positive or negative viewable image is produced is a function of both the emulsion chosen and the photographic processing undertaken. Although light processing is known and employed for specialized applications, in most instances photographic processing to produce a viewable image is accomplished by development of an imagewise exposed photographic element in an aqueous alkaline processing solution. Usually internal latent image forming emulsions are employed in combination with uniform light exposure or, preferably a nucleating agent, to produce direct positive images. Direct positive images can be produced also by employing initially surface fogged silver halide grains which rely on selective development of unexposed grains to produce direct positive images. Internal latent image emulsions can be used to produce negative images by internal development—that is, developing in the presence of iodide ion or a silver halide solvent capable of rendering the internal latent image site accessible to the developing agent. Aside from solarization effects, surface latent image emulsions cannot produce direct positive images, but are extensively used to produce positive color images by reversal processing. Of extreme importance to obtaining commercially attractive photographic images are a large variety of emulsion, photographic element, and processing solution addenda. A succinct summary of radiation sensitive silver halide emulsions, photographic elements, processing solutions, their basic and modifying components, and significant patents and publications describing their features is contained in *Research Disclosure*, Vol. 176, December 1978, Item 17643. *Research Disclosure* is published by Kenneth Mason Publications, Ltd., 8 North Street, Emsworth, Hampshire P010 7DD, England.

The 1-arylisotellurazolo[1,5-a] aromatic tellurazoles of this invention when employed as filter materials can be substituted for conventional filter materials incorporated in silver halide photographic elements. Such materials and their uses are described in *Research Disclosure*, Item 17643, cited above, Item VIII. To illustrate one such application, it is common in multicolor photographic elements to protect the silver halide emulsion layers intended to record green and red exposures from exposure to blue light by locating a blue absorbing filter layer, often referred to as a yellow filter layer, between the green and red recording emulsion layers and a source of exposing radiation. Typically the green and red recording emulsion layers lie between the blue absorbing filter layer and the photographic support. The 1-arylisotellurazolo[1,5-a] aromatic tellurazoles of this invention dispersed in a conventional vehicle, typically a hydrophilic colloid, such as gelatin, can achieve blue absorption in such layers.

In addition to use as filter materials the 1-arylisotellurazolo[1,5-a] aromatic tellurazoles of this invention can be substituted for heterocyclic nuclei in photographic addenda incorporated in emulsion and other layers of silver halide photographic elements. Conventional photographic addenda including stable heterocyclic nuclei include dyes, antifoggants and stabilizers, and nucleating agents, each illustrated by *Research Disclosure*, Item 17643, cited above.

EXAMPLES

The invention can be better appreciated by reference to the following specific examples. Preparations of compounds which are taught from prior publications are labelled preparations while preparations of compounds employed in the process of this invention to produce 1-arylisotellurazolo[1,5-a] aromatic tellurazoles not taught by prior publications are designated examples.

A. Preparation of 2-Phenylazophenyltellurium Trichloride

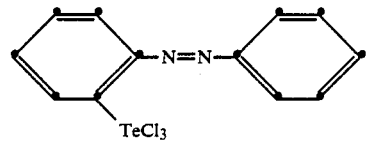

$C_{12}H_9Cl_3N_2Te$     mw=415.18

A two-liter, 3-necked flask was fitted with mechanical stirrer (Teflon ® blade), reflux condenser and nitrogen inlet. A gas outlet from the top of the condenser was connected to a gas bubbler dipping into a magnetically stirred 1000 ml beaker containing 200 ml distilled water and a little phenolphthalein indicator. The system was sufficiently gas tight so that a very gentle stream of nitrogen produced consistent bubbles in the indicator solution.

Into the flask were placed 100 g (0.55 mole) azobenzene, 134 g (0.5 mole) tellurium tetrachloride, and 66 g (0.5 mole) anhydrous aluminum chloride. 1,2-Dichlorobenzene (500 ml) was added, the apparatus closed, the nitrogen flow started, and the mixture stirred until an orange-brown solution was obtained. Five ml of 1N sodium hydroxide were then added to the indicator solution, and the flask contents were heated to reflux with brisk stirring. The start of the reaction was marked by loss of the indicator color. Measured volume increments of 1N sodium hydroxide were then added to the beaker each time the indicator color discharged. Incremental volume and elapsed time of addition are tabulated below:

| Time Minutes | Vol. in NaOH ml |
| --- | --- |
| 0 | 5 |
| 6.5 | 50 |
| 13.0 | 100 |
| 20.0 | 150 |
| 28.0 | 200 |
| 36.5 | 250 |
| 46.0 | 300 |
| 54.0 | 350 |
| 70.0 | 400 |
| 85.0 | 450 |
| 94.0 | 475 |

Boiling under reflux was continued until 475 ml 1N sodium hydroxide had been consumed. The flask contents were then permitted to cool to about 80° C. Methyl alcohol was then added very slowly to the rapidly stirred solution until the initial vigorous reaction ceased. A total of 500 ml methanol was then added and the mixture cooled in ice for more than one hour. The heavy granular crystalline precipitate was collected by filtration and washed with methanol until the methanol filtrate was pale yellow.

The light brown glittering crystals were dried in vacuum. A yield of 130.3 g (63% of theory), m.p. 261°–263° C. was obtained. The product contained small amounts of oxides that were removed by recrystallization from 1,2-dichlorobenzene. Elemental analyses of the recrystallized product were in agreement with the structural formula.

B. Preparation of 3,4-Dimethoxyphenyltellurium Trichloride

$C_8H_9Cl_3O_2Te$    mw=371.13

1,2-Dimethoxybenzene (veratrole, 13.8 g=0.1 mole) and tellurium tetrachloride (26.9 g=0.1 mole) were heated in chloroform (120 ml) for 2 hours under reflux and with stirring. After 30 minutes yellow crystals started to precipitate. The product (25.2 g, 67.9% of theory) was collected by filtration and dried in a vacuum oven, m.p. 162°–163° C. (dec. with gas evolution). The mass spectra were in agreement with that of the structural formula.

C. Preparation of Bis(3,4-dimethoxyphenyl)ditelluride

$C_{16}H_{18}O_4Te_2$    mw=529.42

3,4-Dimethoxyphenyltellurium trichloride (37.2 g=0.1 mole) was dissolved in absolute ethanol (500 ml), and the slightly turbid solution was filtered. To the rapidly stirred solution was added, at room temperature, 50% aqueous hypophosphorous acid (30 ml, ≈0.3 mole) as rapidly as possible. There was a brief appearance of a brown solution color, before the entire solution set to a mass of black fibrous crystals. The product was collected after 15 minutes by filtration using rubber dam to compact the highly solvated crystal mass. The product was washed with water and then air dried to yield 25.2 g. 95% of theory, black fibrous crystals, m.p. 134°–136° C. Recrystallization from isopropanol raised the m.p. to 136°–139° C. C, H and Te elemental analyses were in agreement with the structural formula.

λ-max=305 nm    ε-max=1.006×10⁴

EXAMPLE 1

1-Chloro-5,6-dimethoxy-2,1,3-benzoxatellurazole-N-oxide

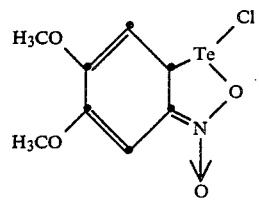

$C_8H_8ClNO_4Te$    mw=345.21

A. By nitration of product of Preparation C

Bis(3,4-dimethoxyphenyl)ditelluride (10 g=0.018 mole) was added in small portions to 70 mole percent nitric acid (15 ml) with stirring and chilling in ice. The material dissolved rapidly with emission of nitrous fumes. The mixture was then warmed at ≈40° C. for 30 minutes and subsequently stirred at room temperature for one hour. Emission of orange fumes was no longer observed. Water (150 ml) was then added to the orange solution resulting in a yellow precipitate, which (5 g) was mixed with ethanol (100 ml) and concentrated hydrochloric acid (20 ml), then diluted with water to 200 ml (just prior to occurrence of precipitation). Hypophosphorous acid (5 ml of 50 mole percent) was then added. During 15 minutes of stirring at room temperature, a deep red precipitate appeared which was collected by filtration. The product was recrystallized from absolute ethanol (450 ml) to give red prisms (2.5 g), m.p. 197°–200° C. The yield by this procedure calculated to be ≈32%.

B. By nitration and reduction of product of Preparation B 3,4-Dimethoxyphenyltellurium trichloride (74 g=0.2 mole) was suspended in glacial acetic acid (200 ml) in a 1500 ml Erlenmeyer flask. Nitric acid (18 g of 70%=0.2 mole) was added gradually to the stirred mixture, which caused formation of a clear, red solution and a mildly exothermic reaction. Stirring was continued for one hour at room temperature, then ethanol (1000 ml) and hypophosphorous acid (24.0 g of 50 weight percent aqueous) were added in order. Over a period of 30 minutes there occurred crystallization of a red solid, which was collected by filtration to give 47.3 g, 68.8% of theory, m.p. 199°–200° C. The material was identical to product isolated by procedure A. Elemental analyses were in agreement with that calculated for the structural formula.

EXAMPLES 2–5

Examples 2 through 5 illustrate the preparation of compounds according to the following general formula

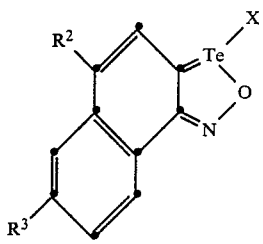

EXAMPLE 2

3-Chloronaphth[2,1-c]-1,2,5-oxatellurazole, $R^3=R^2=H$, $X=Cl$

$C_{10}H_6ClNOTe$    mw=319.22

Tellurium dioxide (80 g, 0.5 mole) was dissolved in concentrated hydrochloric acid (200 ml, 2.0 moles) with stirring. When solution was complete, a suspension of hydroxylamine hydrochloride (69 g, 1.0 mole) in ethyl alcohol (300 ml) was added. When all solid was dissolved, α-tetralone (73 g, 0.5 mole) in ethyl alcohol (1200 ml) was added. The clear reaction mixture rapidly turned red and dark crystals began to form within an hour. After the reaction mixture had been kept five days at room temperature, the product was isolated by filtration and dried in a vacuum. Yield 123.2 g.

The product was separated from elemental tellurium by continuous extraction with dichloromethane in a Soxhlet extractor, using about 1300 ml of solvent. Chilling the extract yielded a first crop of 84.9 g. Diluting the filtrate with twice its volume of heptane yielded a second crop of 6.1 g. The combined yield of 91.0 g represented a 57% yield. mp. 182°–183° C. λ-max (in pyridine) was 503 nm. ε-max=0.82×10⁴. C, H, Cl, N, O and The elemental analyses results and the mass spectra were in agreement with those expected for the structural formula.

EXAMPLE 3

3-Bromonaphth[2,1c]-1,2,5-oxatellurazole, $R^3 = R^2 = H$, $X = Br$ $C_{10}H_6BrNOTe$    mw = 363.68

Alpha-tetralone oxime (24 g=0.05 mole), tellurium dioxide (35 g=0.22 mole), lithium bromide (60 g), and acetic acid (350 ml) were combined, and the mixture was heated to a gentle boil for 20 minutes. The precipitated solid was collected by filtering the reaction mixture hot and washing the product with water to give 38.9 g, 71% of theory, of a deep maroon solid. The product was recrystallized from carbon tetrachloride (m.p. 183°–185° C.). Elemental analyses and the mass spectra were in agreement with the those expected for structural formula.

EXAMPLE 4

3-Chloro-5-methylnaphth[2,1-c]-1,2,5-oxatellurazole, $R^3 = H$, $R^2 = CH_3$, $X = Cl$ $C_{11}H_8ClNOTe$    mw = 333.24

Tellurium dioxide (79.5 g=0.5 mole) was dissolved in concentrated hydrochloric acid (200 ml). Hydroxylamine hydrochloride (35 g=0.5 mole) was added and then ethanol to bring the total volume to 2000 ml. To the slightly turbid solution was added 4-methyl-α-tetralone (80 g=0.5 mole) and the stirred mixture heated briefly to boil. The clear deep red solution was then kept overnight at room temperature. The solid mass of crystalline product was collected, washed well with water and dried in a vacuum oven at 90° C. to give a first crop (111.1 g) of dark red needles. The filtrate was heated once again and kept at room temperature for 24 hours. A second crop of 14.3 g crude product was obtained. The well-dried product was placed into a Soxhlet thimble and extracted with methylene chloride. The majority of purified product crystallized from the solvent during the course of the extraction to give a yield of 97.0 g=58.3% of theory, m.p. 196°–198' C. Elemental analyses results were in agreement with the structural formula. The ultraviolet and visible spectra in dichloromethane showed three maxima.

| λ-max 507 nm | ε-max = 1.21 × 10⁴ |
|---|---|
| λ-max 300 nm | ε-max = 1.06 × 10⁴ |
| λ-max 256 nm | ε-max = 2.30 × 10⁴ |

EXAMPLE 5

3-Chloro-7-methoxynaphth[2,1-c]-1,2,5-oxatellurazole, $R^3 = OCH_3$, $R^2 = H$, $X = Cl$ $C_{11}H_8ClNO_2Te$    mw = 349.24

This compound was prepared in the same general way as the corresponding compound of Example 4, except that 6-methoxy-α-tetralone (88.1 g=0.5 mole) was used as the starting ketone. The step of heating of the reaction mixture to boil and then keeping it at room temperature was repeated three times, giving a combined crude yield of 84.8 g. Recrystallization by Soxhlet extraction with dichloromethane gave 72.5 g, 41.5% yield, of small dark needles (m.p. 237°–239° C.). Elemental analyses results were in agreement with the structural formula. The ultraviolet and visible spectra in dichloromethane showed four maxima.

| 510 nm | ε-max = 0.89 × 10⁴ |
|---|---|
| 454 nm | ε-max = 0.93 × 10⁴ |
| 312 nm | ε-max = 0.81 × 10⁴ |
| 245 nm | ε-max = 2.63 × 10⁴ |

EXAMPLE 6

1-Chloroacenaphtho[5,1-b]-2,1,5-oxatellurazole

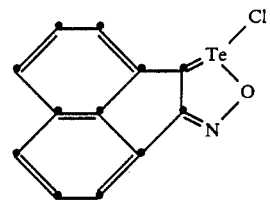

Acenaphthylen-1-one (83.5 g, 0.05 mole), hydroxylamine hydrochloride (35 g, 0.05 mole), and tellurium dioxide (80 g, 0.05 mole) were combined in ethanol (3 l). The mixture was heated to reflux and maintained at that temperature for an hour. It was then allowed to cool to room temperature and stirring at room temperature continued for 12 days. The solid was isolated by filtration, washed with ethanol, and air dried. Yield of brown powder was 106 g. This was extracted with toluene in a Soxlet extractor. The yield of product was 67.6 g, 46% of theory. The ultraviolet and visible spectra in dichloromethane solution showed four maxima, at 489.6, 429, 372, and 316 nanometers.

EXAMPLES 7–11

These examples refer to novel 1,1,1-trihalo (substituted) 2,1,4-benzotellurazinium, inner salts.

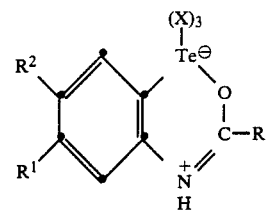

EXAMPLE 7

1,1,1-Trichloro-6-methoxy-3-methyl-2,1,4-benzoxatellurazinium, inner salt, $R^1 = OCH_3$, $R^2 = H$, $R = CH_3$, $X = Cl$ $C_9H_{10}Cl_3NO_2Te$    mw = 398.05

3-Methoxyacetanilide, (34 g=0.2 mole) and tellurium tetrachloride (54 g=0.2 mole) were jointly stirred into chloroform (100 ml) in a 500 ml Erlenmeyer flask. After an initial solution had been formed, the mass set solid with a fine yellow precipitate. The mixture was immersed in an oil bath kept at 115° C. The mixture was manually stirred until all solids had redissolved or melted. After most of the chloroform had evaporated, there resulted a clear yellow melt that rapidly became opaque while gaseous HCl was being emitted. The temperature was raised to 120° C. and heating continued with occasional manual stirring until the entire mass had set to a brittle solid. The reaction was terminated after 2 hours. Ethanol was added to the still hot reaction mixture to disperse the product. Recrystallization from ethanol (1300 ml) yielded colorless needles (47.1 g, 59% of theory), m.p. 245°–246° C.

C, H, N and Te elemental analyses were in agreement with those calculated for the structural formula.

EXAMPLE 8

1,1,1-Trichloro-3,6-dimethyl-2,1,4-benzoxatellurazinium, inner salt, $R=R^1=CH_3$, $R^2=H$, $X=Cl$ $C_9H_{10}Cl_3NOTe$     mw=382.05

3-Methylacetanilide (m-acetotoluidide) (82 g=0.55 mole) and tellurium tetrachloride (148 g, 0.55 mole) were combined with chloroform (300 ml) and the mixture heated for 20 hours in an oil bath kept at 115° C. with continuous removal of HCl. The hot reaction product was dispersed in ethanol (200 ml) and the product collected by filtration to give a yield of 149 g, 71% of theory, colorless prisms, m.p. <300° C. For analyses the compound was recrystallized from boiling acetonitrile.

The elemental analyses were in agreement with those expected for the structural formula.

EXAMPLE 9

1,1,1-Trichloro-3,6,7-trimethyl-2,1,4-benzoxatellurazinium, inner salt, $R=R^1=R^2=CH_3$, $X=Cl$ $C_{10}H_{12}Cl_3NOTe$     mw=396.07

3,4-Dimethylacetanilide (56 g=0.37 mole) was combined with $TeCl_4$ (100 g, 0.37 mole) in acetonitrile (100 ml) and immersed in an oil bath, first for one hour at 120° C. and then for 3 more hours at 130° C. Additional acetonitrile was added, and the partial solution was chilled. The product was collected by filtration to give 74.7 g, 52% of theory, colorless crystals, m.p. <300° C. after darkening at <280° C. Recrystallization from acetonitrile required 400 ml solvent for 15 g of the substance. C, H, Cl, N and Te elemental analyses were in agreement with those expected for the structural formula.

EXAMPLE 10

1,1,1-Trichloro-3-methyl-6-methylthio-2,1,4-benzoxatellurazinium, inner salt, $R=CH_3$, $R^1=SCH_3$, $R^2=H$, $X=Cl$ $C_9H_{10}Cl_3NOSTe$     mw=413.95

3-Methylthioacetanilide (68 g=0.37 mole), prepared by acetylation of commercial 3-methylthioaniline, was combined with $TeCl_4$ (100 g=0.37 mole) in chloroform (100 ml). The mixture was heated for 3 hours in an oil bath kept at 130° C., then introduced hot into acetonitrile (300 ml), chilled, and filtered. A crystalline solid yielding 68 g, 49% of theory was obtained. For analysis the material was recrystallized from boiling acetonitrile (100 ml dissolves ≃4 g) with the aid of decolorizing charcoal and was recovered as lustrous, pale yellow prisms, m.p. 251°–253° C. The elemental analyses were in agreement with those expected for the structural formula.

EXAMPLE 11

1,1,1-Trichloro-6-hydroxy-3-methyl-2,1,4-benzoxatellurazinium, inner salt, $R=CH_3$, $R^1=OH$, $R^2=H$, $X=Cl$ $C_8H_8Cl_3NO_2Te$     mw=383.95

3-Hydroxyacetanilide (60 g=0.4 mole) and $TeCl_4$ (107.6 g=0.4 mole) were combined in acetonitrile (80 ml) and the mixture immersed for 2 hours in an oil bath maintained at 120° C. To the hot melt was then added enough acetonitrile to make a paste. The mixture chilled overnight and filtered with suction to give 86.5 g, 56% of theory, colorless crystalline solid. For analysis this was recrystallized from hot acetonitrile, where 25 g required 150 ml of solvent and gave a recovery of 10 g colorless needles, m.p 247°–248° C. The elemental analyses were in agreement with that expected for the structural formula.

D. Preparation of Bis(2-acetamido-4-methoxyphenyl)ditelluride $C_{18}H_{20}N_2O_4Te_2$     mw=583.23

1,1,1-Trichloro-6-methoxy-3-methyl-2,1,4-benzoxatellurazinium, inner salt (Example 11) (5.0 g=0.0125 mole) was dissolved in 50% aqueous ethanol (200 ml). The solution heated to boil, and hydrazine (1 ml) was added with stirring. The deep orange solution was cooled slowly to room temperature to deposit fibrous needles which, upon filtration and drying, yielded a tan solid (3.25 g, 89% of theory), m.p. 181°–182° C.

EXAMPLES 12–17

Examples 12 through 17 illustrate the preparation of benzotellurazolium hydro salts.

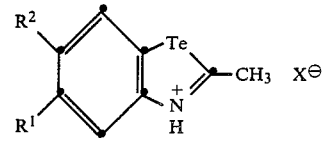

EXAMPLE 12

5,6-Dimethoxy-2-methylbenzo-3H-tellurazolium Chloride, $R^1=R^2=OCH_3$, $X=Cl$ $C_{10}H_{12}ClNO_2Te$     mw=341.26

1-Chloro-5,6-dimethoxy-2,1,3-benzoxatellurazole-N-oxide (Example 1) (103 g=0.3 mole) was suspended in a mixture of tetrahydrofuran (1000 ml) and methanol (150 ml) using a 3 liter, 3 necked flask fitted with a stirrer, a nitrogen inlet, a reflux condenser, and a powder addition funnel. Under nitrogen, sodium borohydride (61.5 g–1.6 mole) was added gradually to the stirred solution until the color was a pale cream. The amount of borohydride was determined empirically by the disappearance of the starting material red color. The reaction mixture was then chilled, and acetic anhydride was added until the color had turned a bright orange. This required 41.3 g=0.4 mole acetic anhydride. The reaction was permitted to proceed for 10 minutes, and then concentrated hydrochloric acid (300 ml) was added in one portion. The mixture turned black immediately, indicating that considerable quantities of tellurium had been generated.

The black mixture was stirred for another 30 minutes, then filtered to collect the precipitate. The solid was washed briefly with dichloromethane and air dried. The crude product was then added to 1200 ml boiling methanol containing a little hydrochloric acid and filtered hot with the aid of Celite ® diatomaceous earth. The filtrate was chilled overnight to give pale grey crystals (15.6 g). Two more crops of product were extracted from the black solid, giving a total yield of 21.34 g, 19.9% of theory. For further purification, the material was recrystallized from boiling water containing a little hydrochloric acid. The pale cream colored needles did not have a distinct melting point, but decomposed gradually <150° C.

EXAMPLE 13

5-Methoxy-2-methyl-3H-benzotellurazolium Chloride, $R^1=OCH_3$, $R^2=H$, $X=Cl$ $C_9H_{10}ClNOTe$    mw=311.24

1,1,1-Trichloro-6-methoxy-3-methyl-2,1,4-benzoxatellurazinium, inner salt (Example 7) (40 g=0.1 mole) was suspended in methanol (400 ml), and a solution of sodium hydroxide (8.0 g=0.2 mole) in water (75 ml) was added. This formed a clear solution which was placed into a vessel fitted with a stirrer, a nitrogen inlet, and a condenser. Under nitrogen, sodium borohydride (10.6 g, 0.28 mole) was added in small increments until the solution no longer turned red or orange with further additions, eventually turning colorless. Partway into the reduction, the mixture solidified, but liquified again as the reduction progressed. To the suspension, which had been cooled to ≃10° C., was then added concentrated hydrochloric acid (100 ml) in one portion. The precipitate was filtered after 15 minutes (yield 42 g dark solid), and the filtrate was chilled for a second crop of 12 g solids. The first crop was recrystallized from 700 ml of hot water containing a little hydrochloric acid. The recovery was 16.1 g of almost white needles. The second crop also contained sodium chloride. It was recrystallized from 125 ml methanol, also containing a little hydrochloric acid, to give 3.6 g product. The combined yield of 19.7 g represented 63% of theory. For analysis, the material was crystallized once more from acidic methanol, 105° C. (sinter), 130°-135° C. (turned black), no clear melt <270° C.

EXAMPLE 14

2,5-Dimethyl-3H-benzotellurazolium Chloride, $R^1=CH_3$, $R^2=H$, $X=Cl$ $C_9H_{10}ClNTe$    mw=295.24

1,1,1-Trichloro-3,6-dimethyl-2,1,4-benzoxatellurazinium, inner salt (Example 8) (17.3 g=0.05 mole) was dissolved in a mixture of methanol (300 ml) and 1N sodium hydroxide (100 ml, 0.1 mole) in a vessel fitted with a nitrogen inlet, a condenser, and a magnetic stirrer. Through the condenser was added sodium borohydride until further addition no longer produced a transient orange color. This required about 3.0 g. The mixture was stirred for a few minutes under nitrogen, then concentrated hydrochloric acid (100 ml) was added in one portion. The mixture was clarified by filtration with Celite ®, then evaporated under reduced pressure to 200 ml, again filtered from inorganic salts and chilled overnight. Filtration yielded 9.15 g of colorless solid, which was rinsed with isopropanol and air dried. The material was not pure and contained inorganic salt contaminants.

EXAMPLE 15

2,5,6-Trimethyl-3H-benzotellurazolium Chloride, $R^1=R^2=CH_3$, $X=Cl$ $C_{10}H_{12}ClNTe$    mw=309.25

1,1,1-Trichloro-3,6-7-trimethyl-2,1,4-benzoxatellurazinium, inner salt (Example 9) (39.6 g=0.1 mole) was placed into 400 ml of methanol in a 1000 ml, three necked flask fitted with a stirrer, a nitrogen inlet, a condenser, and a powder addition funnel. Sodium hydroxide (8.0 g=0.2 mole) in water (30 ml) was added, followed by sodium borohydride (8.56 g=0.225 mole) until the reduction mixture was a pale brown. This required heating to aid in dissolving the starting material and the initial reduction products. When the reduction was complete, the mixture was cooled to about 10° C., and concentrated hydrochloric acid (100 ml) was added in one portion. There was a granular black precipitate, which was removed by filtration. The filtrate was evaporated in vacuum to ≃250 ml, diluted with water to twice the volume, and stirred until crystallization was complete. A yield of 29.5 g, 94.8% of theory, was obtained. After two recrystallizations from methanol, the salt melted at 180°-184° C. (dec.).

EXAMPLE 16

2-Methyl-5-methylthio-3H-benzotellurazolium Chloride, $R^1=SCH_3$, $R^2=H$, $X=Cl$ $C_9H_{10}ClNSTe$    mw=327.30

1,1,1-Trichloro-3-methyl-6-methylthio-2,1,4-benzotellurazinium, inner salt (Example 10) (20.7 g=0.05 mole) was placed in methanol (200 ml), and sodium hydroxide (4 g=0.1 mole) dissolved in water (10 ml) was added. The material did not completely dissolve. Sodium borohydride was added in portions with stirring under a nitrogen atmosphere. The starting material underwent vivid color changes to orange and then to blue with the addition of each portion of reducing agent. The mass became difficult to stir. Eventually, the reaction mixture became more liquid, though the orange color kept returning after each portion was added, as the rather insoluble starting material underwent the first reduction step. The reaction mixture was kept overnight under an atmosphere of nitrogen. The reduction was continued the next day by heating the mixture to near reflux temperature while sodium borohydride was being added. When the stage was reached where the reaction turned colorless after a portion was added and the orange color did not return upon further stirring (after the addition of 6.65 g=0.175 mole sodium borohydride), the mixture was cooled to ≃10° C. and concentrated hydrochloric acid (50 ml=0.5 mole) was added in one portion. The mixture turned orange, then yellow, and a copious beige precipitate formed. This was stirred for 45 minutes and then collected by filtration to yield 27.5 g solids. On recrystallization from methanol (300 ml), using Celite ® to clarify the solution, there were obtained 13.5 g, 81.9% of theory, cream colored needles, m.p. 130°-145° C. (dec.).

EXAMPLE 17

5-Hydroxy-2-methyl-3H-benzotellurazolium Chloride, $R^1=OH$, $R^2=H$, $X=Cl$ $C_8H_8ClNOTe$    mw=297.23

1,1,1-Trichloro-6-hydroxy-3-methyl-2,1,4-benzoxatellurazinium, inner salt (Example 11) (19.2 g=0.05 mole) was dissolved in methanol (200 ml) with addition of sodium hydroxide (4 g) in water (20 ml). The reduction was carried out under a nitrogen atmosphere, using sodium borohydride (4.3 g=0.11 mole), after the addition of which the solution became clear. The reaction mixture was cooled to ≃10° C., and concentrated hydrochloric acid (65 ml) was added in one portion. Considerable black precipitate (11.7 g) formed, which was collected by filtration. The filtrate was evaporated to 50 ml and chilled to give a second crop (12.3 g). The products were recrystallized from isopropanol to give a combined yield of 9.45 g, 63.9% of theory, cream colored powder, m.p. 125°-132° C. (dec.).

EXAMPLES 18-25

Examples 18 through 25 illustrate the preparation of benzotellurazoles.

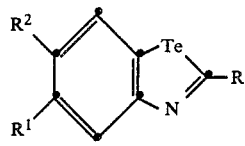

EXAMPLE 18

2-Methylbenzotellurazole, $R=CH_3$, $R^1=R^2=H$ $C_8H_7NTe$    mw=244.74

A mixture of 2-phenylazophenyltellurium trichloride (Preparation A) (20.7 g, 0.05 mole) and ethanol (200 ml) was placed in a 1 liter, 3 necked flask fitted with a nitrogen inlet, a powder addition funnel, and a reflux condenser. To the magnetically stirred mixture was added, under nitrogen, sodium borohydride (7.5 g, 0.2 mole) in increments at a rate sufficient to generate an elevated temperature. When the reaction mixture was nearly colorless the powder funnel was replaced by a stopper, taking care not to interrupt the flow of nitrogen. The flask was then chilled in an ice bath to 5° C. Acetic anhydride (5.5 g, 0.054 mole) was then added, with continued stirring and at such a rate that a temperature of 10° C. was not exceeded in the flask.

The mixture was stirred for another 20 minutes in the ice bath and then 50 ml concentrated aqueous hydrochloric acid was added rapidly. The mixture was stirred for about 10 minutes at room temperature. A black precipitate, which formed during the acid addition, was removed by filtration, washed with ethanol, and discarded, leaving a yellow filtrate.

The yellow filtrate was concentrated under reduced pressure with a bath temperature of about 45° C. When the volume was about 75 ml, the liquid was diluted with water to about 200 ml. The warm solution was clarified by filtration over Celite® diatomaceous earth and then chilled in ice for two hours. A fluffy, crystalline solid (10.5 g) was collected by filtration. The solid was suspended in water (200 ml), and aqueous ammonium hydroxide was added until precipitation appeared to be complete. The somewhat gummy product was collected by filtration, dried superficially in a stream of air and then recrystallized from about 50 ml of isopropanol using charcoal and Celite® to give a clear filtered solution. The compound crystallized in rod-like needles, mp 93°-95° C., yield 5.0 g, 41% of theory. Another 0.8 g was obtained from the acidic filtrate by precipitation with ammonia and subsequent diethyl ether extraction.

EXAMPLE 19

5,6-Dimethoxy-2-methylbenzotellurazole, $R=CH_3$, $R^1=R^2=OCH_3$ $C_{10}H_{11}NO_2Te$    mw=304.80

5,6-Dimethoxy-2-methylbenzotellurazolium chloride (Example 12) (10 g) was ground with an equal quantity of sodium bicarbonate and a little water in a mortar until evolution of carbon dioxide ceased. The product was collected by filtration, washed with water and dried in a vacuum to yield ≃8.5 g of colorless powder, m.p. 78°-80° C. Slow crystallization from cyclohexane yielded well defined prisms, m.p. 80°-83° C. The mass spectra and nuclear magnetic resonance spectra were in agreement with that expected for the structural formula.

EXAMPLE 20

5-Methoxy-2-methylbenzotellurazole, $R=CH_3$, $R^1=OCH_3$, $R^2=H$ $C_9H_9NOTe$    mw=274.77

5-Methoxy-2-methylbenzotellurazolium chloride (Example 13) (3.7 g=0.012 mole) was suspended in water, sodium bicarbonate in excess of that stoichiometrically required was added, and the free base product was extracted with diethyl ether. After washing with saturated sodium sulfate solution, the organic phase was dried and evaporated under reduced pressure to give a residual oil (3.2 g) which was identified by its nuclear magnetic resonance spectra. C, H, N, O and Te elemental analyses were in agreement with that expected for the structural formula.

EXAMPLE 21

2,5-Dimethylbenzotellurazole, $R=R^1=CH_3$, $R^2=H$ $C_9H_9NTe$    mw=258.69

2,5-Dimethylbenzotellurazolium chloride (Example 14) (3.5 g) was treated in an aqueous suspension with sodium bicarbonate in excess of that stoichiometrically required. The free base product was isolated by extraction with diethyl ether and evaporation to dryness. The residue was recrystallized from ≃50 ml isopropanol to yield 1.7 g colorless needles, m.p. 126°-128° C.

EXAMPLE 22

2,5,6-Trimethylbenzotellurazole, $R=R^1=R^2=CH_3$ $C_{10}H_{11}NTe$    mw=272.81

2,5,6-Trimethylbenzotellurazolium chloride (Example 15) was converted to the free base product by treatment with sodium carbonate (15 g) in water and extraction with dichloromethane (300 ml). The extract was washed as described above, dried, and evaporated to a cream colored crystalline residue (10.45 g), which was recrystallized from isopropanol (50 ml). A yield of faintly yellow needles, m.p. 101°-103° C. was obtained.

EXAMPLE 23

2-Methyl-5-methylthiobenzotellurazole, R=CH₃, R¹=SCH₃, R²=H

C₉H₉NSTe  mw=290.84

2-Methyl-5-methylthiobenzotellurazolium chloride (Example 16) (11.5 g=0.035 mole) was suspended in water and sodium bicarbonate in excess of that stoichiometrically required was added. The free base was extracted into dichloromethane. The organic solution was washed with saturated aqueous sodium sulfate, dried, and evaporated in vacuum to a yellow oil (9.06 g). Upon addition of isopropanol (40 ml) the oil crystallized spontaneously to almost white needles to give 8.18 g, 79.8% of theory, m.p. 64°-67° C.

EXAMPLE 24

5-Hydroxy-2-methylbenzotellurazole, R=CH₃, R¹=OH, R²=H

C₈H₇NOTe  mw=260.75

5-Hydroxy-2-methylbenzotellurazolium chloride (Example 17) (7.45 g) was dissolved in warm water (300 ml) and a slurry of sodium bicarbonate (8 g) in water was added slowly. The free base product separated as a cream colored amorphous solid, which was collected by filtration, washed with water, and dried in a vacuum over Drierite ® brand calcium sulfate drying agent, yield 6.3 g. The material was then recrystallized from isopropanol (50 ml) to give a recovery of ≃4.0 g, m.p. 190°-192° C.

EXAMPLES 25-27

Examples 25 through 27 illustrate the preparation of naphthotellurazoles.

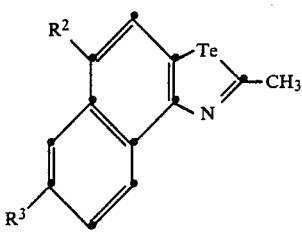

EXAMPLE 25

2-Methylnaphtho[5,1-b]tellurazole, R³=R²=H

C₁₂H₉NTe  mw=294.80

3-Chloronaphth[2,1-c][1,2,5]oxatellurazole (Example 2) (48.0 g=0.15 mole) was suspended in a mixture of methanol (150 ml) and tetrahydrofuran (700 ml) in a two liter 3 necked flask fitted with a mechanical stirrer, a condenser, a powder addition funnel, and a nitrogen inlet. The starting compound was reduced by gradual addition of sodium borohydride (14.2 g=0.375 mole) until the reaction mixture was a pale brown. The powder addition funnel was removed and replaced with a stopper. Final addition of sodium borohydride then took place through the condenser until the appearance of the reduced material no longer changed. The mixture was chilled in ice, still under nitrogen, and acetic anhydride (15.3 g=0.15 mole) was added dropwise. The acetylation was permitted to proceed for about 30 minutes. Concentrated hydrochloric acid (75 ml=0.75 mole) was added in one portion. After stirring the mixture, which now contained a black precipitate, for 30 minutes until it reached room temperature, the precipitate was collected by vacuum filtration, rinsed with tetrahydrofuran and air dried.

The solid was then suspended in 350 ml isopropanol, 25 ml concentrated ammonium hydroxide was added, and the mixture was heated to boiling and filtered rapidly with suction. On cooling, needles (18.65 g, 42% of theory) precipitated from the filtrate. For analyses the product was recrystallized once from isopropanol and exhibited m.p. 101°-103° C. Elemental analyses were in agreement with that expected for the structural formula.

EXAMPLE 26

7-Methoxy-2-methylnaphtho[5,1-b]-tellurazole, R³=OCH₃, R²=H

C₁₃H₁₁NOTe  mw=324.83

3-Chloro-7-methoxynaphth[2,1-c][1,2,5]oxatellurazole (Example 5) (17.45 g=0.05 mole) was reduced, acetylated, and treated with hydrochloric acid using the same method and reagent quantities as given for Example 26. Following the procedure described in Example 26, there were obtained 4.93 g, 30.2% of theory, silvery fluffy needles (m.p. 120°-123° C.). The elemental analyses were in agreement with that expected for the structural formula.

EXAMPLE 27

2,5-Dimethylnaphtho[5,1-b]tellurazole, R³=H, R²=CH₃

C₁₃H₁₁NTe  mw=308.83

3-Chloro-5-methylnaphth[2,1-c][1,2,5]oxatellurazole (Example 4) (16.7 g=0.05 mole) was suspended in a mixture of tetrahydrofuran (THF, 200 ml) and methanol (40 ml) in a 500 ml three necked flask fitted with a nitrogen inlet, a condenser, and a powder addition funnel. Sodium borohydride was added under a nitrogen atmosphere and in small portions until the reaction mixture was a pale orange yellow. This required about 5 to 6 g. The powder addition funnel was then removed and replaced with a stopper. The reaction mixture was then cooled to 5° C. and acetic anhydride (5.1 g=0.05 mole) added slowly through the condenser. The reaction mixture transiently turned a bright orange. Concentrated hydrochloric acid (25 ml) was then added in one portion, the ice bath removed, and the mixture stirred to room temperature. As the reaction mixture warmed up, a crystalline deposit appeared and was collected by filtration. The crystalline deposit was washed with tetrahydrofuran until the filtrate was colorless and clear. The filtrate was then heated to boiling with a mixture of isopropanol (175 ml) and concentrated ammonium hydroxide (25 ml) and filtered hot with Celite ®, the cooled filtrate was diluted with water until crystallization started. A first crop of pale yellow needles (5.06 g), m.p. 110°-112° C. was obtained. A further 1.65 g of product were obtained by two further extractions with the same solvent mixture, giving a total yield of 6.71 g=43.3% of theory. For analysis, the material was recrystallized from isopropanol. This did not change the melting point. Elemental analyses were in agreement with that expected for the structural formula.

EXAMPLE 28

2-Methyl-3H-benzotellurazolium Iodide

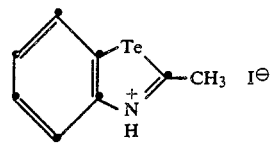

$C_8H_8INTe$   mw=372.67

To a solution of 2-methylbenzotellurazole (Example 18) (0.81 g, 0.0033 mole) in acetone (25 ml), chilled in an ice bath, was added slowly with stirring 55 mole percent hydriodic acid (1 ml). The product began precipitating from solution. After the addition was complete, the mixture was stirred at ice bath temperature for approximately 10 minutes. The solid was isolated by filtration, washed with diethyl ether, and dried under vacuum at room temperature. Yield 1.13 g (92%) of yellow powder, m.p. 209°–211° C. The C, H, and N elemental analyses and the infrared, nuclear magnetic resonance, and mass spectra of the sample were in agreement with that expected for the structural formula.

EXAMPLES 29–58

Examples 29 through 58 illustrate the preparation of N-alkylated benzotellurazolium salts.

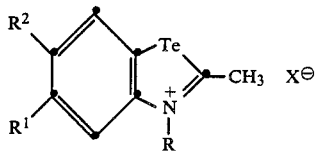

EXAMPLE 29

2,3-Dimethylbenzotellurazolium Trifluoromethanesulfonate, $R=CH_3$, $R^1=R^2=H$, $X=CF_3SO_3$ $C_{10}H_{10}F_3NO_3STe$   mw=408.85

2-Methylbenzotellurazole (Example 18) (10.5 g, 0.043 mole) was dissolved in dry dichloromethane (75 ml). Freshly distilled methyl trifluoromethanesulfonate (7.5 g, 0.045 mole) was added in the solution. An exothermic reaction occurred immediately. After a few minutes a crystalline product separated which was collected by filtration, washed with diethyl ether, and dried. Yield 16.86 g (96%). The pale yellow powder was dissolved in acetone (100 ml) and reprecipitated by adding diethyl ether to the solution until it became turbid. Colorless plates separated on chilling. Yield 15.33 g (87% of theory); mp 160°–162° C.

EXAMPLE 30

5,6-Dimethoxy-2,3-dimethylbenzotellurazolium Trifluoromethanesulfonate, $R=CH_3$, $R^1=R^2=OCH_3$, $X=CF_3SO_3$ $C_{12}H_{14}F_3NO_5STe$   mw=468.90

5,6-Dimethoxy-2-methylbenzotellurazole (Example 19) (4.8 g=0.013 mole) was dissolved in dichloromethane (75 ml), and methyl trifluoromethanesulfonate (2.48 g=1.66 ml=0.013 mole) was added. The solution turned cloudy and crystals started to deposit within a few minutes. Precipitation was completed by addition of diethyl ether. The product was collected by filtration to give 5.5 g, 86.5% of theory, m.p. 210°–234° C. The product was recrystallized from boiling acetone (≃130 ml required) m.p. 242°–243° C.

The quaternary ammonium salts prepared in Examples 31 through 36 below were all prepared in high yield by combining stoichiometric quantities of the respective base and methyl trifluoromethanesulfonate in dichloromethane, precipitating with diethyl ether, and recrystallization from acetone, with diethyl ether in some instances being added. The C, H, F, N and Te elemental analyses and the nuclear magnetic resonance spectra were consistent with that expected for the structures of each of the quaternary salts.

EXAMPLE 31

5-Methoxy-2,3-dimethylbenzotellurazolium Trifluoromethanesulfonate, $R=CH_3$, $R^1=OCH_3$, $R^2=H$, $R^5=CH_3$, $X=CF_3SO_3$ $C_{11}H_{12}F_3NO_4STe$   mw=438.87 m.p. 197°–198° C.

EXAMPLE 32

2,3,5-Trimethylbenzotellurazolium Trifluoromethanesulfonate, $R=R^1=CH_3$, $R^2=H$, $X=CF_3SO_3$ $C_{11}H_{12}F_3NO_3STe$   mw=422.77 m.p. 215°–217° C.

EXAMPLE 33

2,3,5,6-Tetramethylbenzotellurazolium Trifluoromethanesulfonate, $R=R^1=R^2=CH_3$, $X=CF_3SO_3$ $C_{12}H_{14}F_3NO_3STe$   mw=436.91 m.p. 230°–233° C.

EXAMPLE 34

2,3-Dimethyl-5-methylthiobenzotellurazolium Trifluoromethanesulfonate, $R=CH_3$, $R^1=SCH_3$, $R^2=H$, $X=CF_3SO_3$ $C_{11}H_{12}F_3NO_3S_2Te$   mw=454.94 m.p. 195°–195° C.

EXAMPLE 35

5-Hydroxy-2,3-dimethylbenzotellurazolium Trifluoromethanesulfonate, $R=CH_3$, $R^1=OH$, $R^2=H$, $X=CF_3SO_3$ $C_{10}H_{10}F_3NO_4STe$    mw=424.85 m.p. 171°–175° C.

EXAMPLE 36

3-Ethyl-5,6-dimethoxy-2-methylbenzotellurazolium Trifluoromethanesulfonate, $R=C_2H_5$, $R^1=R^2=OCH_3$, $X=CF_3SO_3$ $C_{13}H_{16}F_3NO_5STe$    mw=482.93

(15.7 g, 0.005 mole)
5,6-Dimethoxy-2-methylbenzotellurazole (Example 19) was dissolved in chloroform (150 ml). A stoichiometric amount of ethyl trifluoromethanesulfonate was added, and the solution was refluxed for two hours under a condenser protected with a drying tube. After cooling the solution was poured slowly into cold diethyl ether (700 ml) with rapid stirring. The product crystallized and was collected by filtration. Yield 19.3 g (77.3% of theory).

The quaternary salts of the next three examples were obtained in the same general way as that of Example 36, except as noted, using the appropriate benzotellurazole.

EXAMPLE 37

3-Ethyl-5-methoxy-2-methylbenzotellurazolium Trifluoromethanesulfonate, $R=C_2H_5$, $R^1=OCH_3$, $R^2=H$, $X=CF_3SO_3$ $C_{12}H_{14}F_3NO_4STe$    mw=452.90

The alkylation was carried out in diethyl ether at room temperature. Several crops of crystalline product were collected over three days. Total yield 15.0 g (73% of theory).

EXAMPLE 38

3-Ethyl-2,5,6-trimethylbenzotellurazolium Trifluoromethanesulfonate, $R=C_2H_5$, $R^1=R^2=CH_3$, $X=CF_3SO_3$ $C_{13}H_{16}F_3NO_3STe$    mw=450.93

The product precipitated directly from chloroform. Yield 16.6 g (91% of theory).

EXAMPLE 39

3-Ethyl-2-methyl-5-methylthiobenzotellurazolium Trifluoromethanesulfonate, $R=C_2H_5$, $R^1=SCH_3$, $R^2=H$, $X=CF_3SO_3^\ominus$ $C_{12}H_{14}F_3NO_3S_2Te$    mw=468.96

The product separated from chloroform to which diethyl ether was added to aid precipitation. A gummy residue was recrystallized from ethanol.

EXAMPLES 40–43

Examples 40 through 43 use 2-propen-1-yl trifluoromethanesulfonate in a dry solution of carbon tetrachloride. This was prepared by dissolving trifluoromethanesulfonic anhydride in carbon tetrachloride (about 10 ml of solvent per g of anhydride) and chilling the solution to near 0° C. Under a nitrogen atmosphere a solution of equimolar amounts of 2-propen-1-ol (allyl alcohol) and pyridine in carbon tetrachloride (about 5 ml of solvent per g of anhydride) was added dropwise to the chilled anhydride solution. Stirring was continued for about 30 minutes after the addition was complete, maintaining the nitrogen atmosphere and ice-bath temperature. The reaction mixture was then filtered through a pad of sodium sulfate, and the dried solution was used in the subsequent examples.

EXAMPLE 40

A. 2-Methyl-3-(2-propen-1-yl)benzotellurazolium Trifluoromethanesulfonate, $R=CH_2-CH=CH_2$ $R^1=R^2=H$, $X=CF_3SO_3$ $C_{12}H_{12}F_3NO_3STe$    mw=434.90

The dried solution of 2-propen-1-yl trifluoromethanesulfonate (0.008 mole) in carbon tetrachloride was placed in a dropping funnel and added to a solution of 2-methylbenzotellurazole (Example 18) (1.62 g, 0.0066 mole) in dichloromethane (25 ml) under a nitrogen atmosphere at room temperature. After the addition was complete, stirring was continued for 18 hours. The solid was isolated by filtration, washed with diethyl ether, and dried at room temperature under vacuum. Yield 0.43 g (15%), m.p. 90°–93° C. Infrared, nuclear magnetic resonance, and mass spectra were in agreement with that expected for the structural formula.

B. 2-Methyl-3-(2-propen-1-yl)benzotellurazolium Iodide, $R=CH_2-CH=CH_2$, $R^1=R^2=H$, $X=I$ $C_{11}H_{12}INTe$    mw=412.73

The solvents from the filtrates above were removed under vacuum and the dark orange semisolid redissolved in acetone (about 30 ml). The solution was stirred, chilled, and treated with a saturated solution of sodium iodide in acetone (about 5 ml). The solid was isolated by filtration, washed with acetone, diethyl ether, and dried. Yield 0.52 g (21% of theory) m.p. 205°–207° C. Elemental analyses and nuclear magnetic resonance spectra were in agreement with that expected for the structural formula.

EXAMPLE 41

5,6-Dimethoxy-2-methyl-3-(2-propen-1-yl)benzotellurazolium Trifluoromethanesulfonate, $R=CH_2-CH=CH_2$ $R^1=R^2=OCH_3$, $X=CF_3SO_3$ $C_{14}H_{16}F_3NO_5STe$    mw=494.95

A dried solution of 2-propen-1-yl tri-fluoromethanesulfonate (0.002 mole) in carbon tetrachloride was added dropwise to a solution of 5,6-dimethoxy-2-methylbenzotellurazole (Example 19) (0.50 g, 0.0016 mole) in dichloromethane (25 ml) under a nitrogen atmosphere at room temperature. After the addition was complete, stirring was continued for 7 hours. The solid was isolated by filtration, washed with diethyl ether, and dried at room temperature under vacuum. Yield 0.38 g. A mass spectrogram of the compound was in agreement with that expected for the structural formula.

EXAMPLE 42

5-Methoxy-2-methyl-3-(2-propen-1-yl)benzotellurazolium Trifluoromethanesulfonate,
R=CH$_2$CH=CH$_2$, R$^1$=OCH$_3$, R$^2$=H, X=CF$_3$SO$_3$ C$_{13}$H$_{14}$F$_3$NO$_4$STe    mw=464.92

5-Methoxy-2-methylbenzotellurazole (Example 20) (0.91 g, 0.033 mole), dissolved in dichloromethane (25 ml), was added at room temperature under a nitrogen atmosphere to the solution of 2-propen-1-yl trifluoromethanesulfonate (0.004 mole) from a dropping funnel. The mixture was stirred at room temperature for another 21 hours after the addition was complete, maintaining the nitrogen atmosphere. The solid was isolated by filtration, washed with diethyl ether, and dried at room temperature under vacuum. Yield 0.90 g.

EXAMPLE 43

2,5,6-Trimethyl-3-(2-propen-1-yl)benzotellurazolium Trifluoromethanesulfonate, R=CH$_2$CH=CH$_2$, R$^1$=R$^2$=CH$_3$, X=CF$_3$SO$_3$ C$_{14}$H$_{16}$F$_3$NO$_3$STe    mw=462.94

To a solution of 2,5,6-trimethylbenzotellurazole (Example 22) (9.90 g, 0.0033 mole) in dichloromethane (30 ml) was added the solution of 2-propen-1-yl trifluoromethanesulfonate (0.004 mole) rapidly at room temperature under a nitrogen atmosphere, with good stirring. Solid began separating 10 minutes after the addition was complete. Stirring under a nitrogen atmosphere was continued for about 18 hours. The solid was isolated by filtration, washed with diethyl ether, and dried under vacuum at room temperature. Yield 1.0 g, m.p. 162°–164° C. The mass spectra agreed with the assigned structural formula.

EXAMPLES 44–47

2-Propyn-1-yl trifluoromethanesulfonate was prepared in carbon tetrachloride solution and used as a dried solution in Examples 44 through 47 in the same way that 2-propen-1-yl trifluoromethanesulfonate was prepared and was used in Examples 40 through 43 starting with 2-propyn-1-ol (propargyl alcohol) and trifluoromethanesulfonic anhydride.

EXAMPLE 44

2-Methyl-3-(2-propyn-1-yl)benzotellurazolium Trifluoromethanesulfonate, R=CH$_2$C≡CH, R$^1$=R$^2$=H, X=CF$_3$SO$_3$ C$_{12}$H$_{10}$F$_3$NO$_3$STe    mw=432.87

2-Methylbenzotellurazole (Example 18) (0.81 g, 0.0033 mole) was dissolved in dichloromethane (30 ml). A solution in carbon tetrachloride (25 ml) of 2-propyn-1-yl trifluoromethanesulfonate, prepared as described above, (0.004 mole) was placed in a dropping funnel and added at room temperature under a nitrogen atmosphere to the benzotellurazole solution. The mixture was stirred for about 20 hours after the addition was complete, forming a white solid, which was isolated by filtration, washed with dichloromethane, and dried at room temperature under vacuum. Yield 0.60 g (42% of theory), m.p. 150°–152° C. The infrared, nuclear magnetic resonance and mass spectra were consistent with the structural formula.

EXAMPLE 45

5,6-Dimethoxy-2-methyl-3-(2-propyn-1-yl)benzotellurazolium Trifluoromethanesulfonate,
R=CH$_2$C≡CH, R$^1$=R$^2$=OCH$_3$, X=CF$_3$SO$_3$ C$_{14}$H$_{14}$F$_3$NO$_5$STe    mw=492.92

5,6-Dimethyoxy-2-methylbenzotellurazole (Example 19) (1.0 g, 0.033 mole) was dissolved in dichloromethane (25 ml). The solution of 2-propyn-1-yl trifluoromethanesulfonate, prepared as described above, was added from a dropping funnel under a nitrogen atmosphere. After completion of the addition the mixture was stirred for 16 hours at room temperature. The solid was isolated by filtration, washed with diethyl ether, and dried under vacuum at room temperature. Yield, 1.14 g (70% of theory). The infrared, nuclear magnetic resonance, and mass spectra were in agreement with that expected for the structural formula.

EXAMPLE 46

5-Methoxy-2-methyl-3-(2-propyn-1-yl)benzotellurazolium Trifluoromethanesulfonate,
R=CH$_2$C≡CH, R$^1$=OCH$_3$, R$^2$=H, X=CF$_3$SO$_3$ C$_{13}$H$_{12}$F$_3$NO$_4$STe    mw=462.89

This compound was prepared in the same way and on the same scale as the compound of Example 45, except that 5-methoxy-2-methylbenzotellurazole (Example 20) was used in place of the 5,6-dimethoxy-2-methylbenzotellurazole. Yield 1.23 g, 80% of theory, pale tan powder, m.p. 172°–174° C. (dec). The infrared, nuclear magnetic resonance, and mass spectra were in agreement with that expected for the structural formula.

EXAMPLE 47

2,5,6-Trimethyl-3-(2-propyn-1-yl)benzotellurazolium Trifluoromethanesulfonate, R=CH$_2$C≡CH, R$^1$=R$^2$=CH$_3$, X=CF$_3$SO$_3$ C$_{14}$H$_{14}$F$_3$NO$_3$STe    mw=460.93

This compound was prepared in the same way and on the same molar scale as the compound of Example 45, except that 2,5,6-trimethylbenzotellurazole (Example 22) was used in place of 5,6-dimethoxy-2-methylbenzotellurazole. Yield 1.10 g (72% of theory) cream colored powder, m.p. 189°–192° C. dec. The infrared, nuclear magnetic resonance, and mass spectra were in agreement with that expected for the structural formula.

EXAMPLES 48–51

Ethoxycarbonylmethyl trifluoromethanesulfonate was prepared in carbon tetrachloride solution and used as a dried solution in Examples 48 through 51 in the same way that 2-propen-1-yl trifluoromethanesulfonate was prepared and used in Examples 40 through 43, starting with hydroxyacetic acid, ethyl ester (ethyl glycolate).

EXAMPLE 48

3-Ethoxycarbonylmethyl-2-methylbenzotellurazolium Trifluoromethanesulfonate,

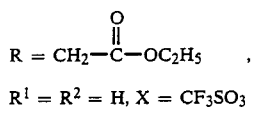

$R^1 = R^2 = H, X = CF_3SO_3$ $C_{13}H_{14}F_3NO_5STe$  mw=480.91

2-Methylbenzotellurazole (Example 18) (0.81 g, 0.0033 mole) was dissolved in dichloromethane (30 ml). The solution of ethoxycarbonylmethyl trifluoromethanesulfonate (0.004 mole) in carbon tetrachloride prepared as described above, was placed in a dropping funnel and added to the benzotellurazole solution at room temperature under a nitrogen atmosphere. After the addition was complete, the mixture was stirred at room temperature, while maintaining a nitrogen atmosphere for 22 hours. The solid was isolated by filtration and dried at room temperature under vacuum. Yield was 0.62 g (39% of theory) of a white powder, m.p. 156°–158° C. The C, H, N and S elemental analyses and the infrared, nuclear magnetic resonance, and mass spectra were all in agreement with that expected for the structural formula.

EXAMPLE 49

3-Ethoxycarbonylmethyl-5,6-dimethoxy-2-methylbenzotellurazolium Iodide,

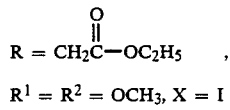

$R^1 = R^2 = OCH_3, X = I$ $C_{14}H_{18}INO_4Te$  mw=518.81

5,6-Dimethoxy-2-methylbenzotellurazole (Example 19) (1.22 g, 0.004 mole) was dissolved in dichloromethane (25 ml). The solution of ethoxycarbonylmethyl trifluoromethanesulfonate (0.004 mole) in carbon tetrachloride, which was prepared as described above, was placed in a dropping funnel and added slowly at room temperature and under a nitrogen atmosphere to the benzotellurazole solution. The reaction mixture was filtered to remove the small amount of solid that had formed. The solvents were removed from the filtrate under reduced pressure, and the residue was redissolved in acetone. The solution was treated with saturated sodium iodide in acetone. This was stirred for 15 minutes. After crystallization began, the mixture was chilled and then filtered. The solid was washed with diethyl ether and dried at room temperature under a vacuum. Yield 0.45 g (22% of theory) of pale yellow crystals, m.p., 184°–186° C. The infrared, nuclear magnetic resonance, and mass spectra were in agreement with that expected for the structural formula.

EXAMPLE 50

Ethoxycarbonylmethyl-5-methoxy-2-methyl-3-benzotellurazolium Iodide,

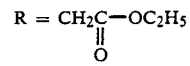

$R^1 = OCH_3, R^2 = H, X = I$ $C_{13}H_{16}INO_3Te$  mw=488.78

This compound was prepared in the same way and on the same scale as the compound of Example 49, except that 5-methoxy-2-methylbenzotellurazole (Example 20) was used in place of 5,6-dimethoxy-2-methylbenzotellurazole. Yield 0.45 g (28% of theory) of a greenish yellow powder, m.p. 215°–217° C. (dec). The infrared, nuclear magnetic resonance, and mass spectra were in agreement with that expected for the structural formula.

EXAMPLE 51

3-Ethoxycarbonylmethyl-2,5,6-trimethylbenzotellurazolium Trifluoromethanesulfonate,

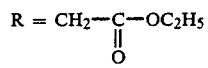

$R^1 = R^2 = CH_3, X = CF_3SO_3$ $C_{15}H_{18}F_3NO_5STe$  mw=508.96

2,5,6-Trimethylbenzotellurazole (Example 22) (0.90 g, 0.0033 mole) was dissolved in dichloromethane (25 ml). A solution of ethoxycarbonylmethyl trifluoromethanesulfonate was placed in a dropping funnel and added rapidly to the benzotellurazole solution, at room temperature and under a nitrogen atmosphere. Stirring was continued for 20 hours after the addition was complete at room temperature while maintaining a nitrogen atmosphere. The solid was isolated by filtration, washed with diethyl ether, and dried at room temperature under vacuum. Yield 0.83 g (49% of theory) of gray-white powder, m.p. 177°–179° C. (dec). The infrared, nuclear magnetic resonance, and mass spectra were in agreement with that expected for the structural formula.

An additional quantity of the compound as the iodide salt was obtained by removing the solvents from the filtrate under reduced pressure, redissolving the residue in acetone, and treating with a saturated solution of sodium iodide in acetone. The yellow solid which formed was isolated by filtration, washed, and dried as before. Yield 0.30 g, m.p. 222°–224° C. (dec.). The various spectra were also in agreement with that expected for the structural formula.

EXAMPLES 52–54

Benzyl trifluoromethanesulfonate was prepared in carbon tetrachloride solution and used as a dried solution in Examples 52 through 54, in the same way the 2-propen-1-yl trifluoromethanesulfonate was prepared and used in Examples 40 through 43, starting with benzyl alcohol and trifluoromethanesulfonic anhydride.

EXAMPLE 52

3-Benzyl-2-methylbenzotellurazolium Trifluoromethanesulfonate,

R = CH$_2$— 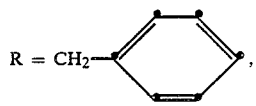,

R$^1$ = R$^2$ = H, X = CF$_3$SO$_3$

C$_{16}$H$_{14}$F$_3$NO$_3$STe    mw = 484.94

2-Methylbenzotellurazole (Example 18) (0.81 g), 0.0033 mole) was dissolved in dichloromethane (25 ml). The solution of benzyl trifluoromethanesulfonate (0.004 mole) in carbon tetrachloride, prepared as described above, was placed in a dropping funnel and added at room temperature under a nitrogen atmosphere to the benzotellurazole solution. Stirring was continued for 18 hours at room temperature after the addition was complete, maintaining a nitrogen atmosphere. The solid was isolated by filtration, washed with diethyl ether, and dried at room temperature under a vacuum. Yield 0.30 g (19% of theory) of a white powder, m.p. 120°–122° C. The infrared, nuclear magnetic resonance, and mass spectra of this compound were in agreement with that expected for the structural formula.

EXAMPLE 53

3-Benzyl-5,6-dimethoxy-2-methylbenzotellurazolium Trifluoromethanesulfonate,

R = CH$_2$— 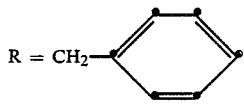,

R$^1$ = R$^2$ = OCH$_3$, X = CF$_3$SO$_3$

C$_{18}$H$_{18}$F$_3$NO$_5$STe    mw = 544.99

This compound was prepared in the same way and on the same scale as the compound of Example 52, except that 5,6-dimethoxy-2-methylbenzotellurazole (Example 19) was used in place of 2-methylbenzotellurazole. Yield 0.50 g of a pale gray powder, m.p. 179°–182° C. (dec). The infrared, nuclear magnetic resonance, and mass spectra were in agreement with that expected for a mixture of desired compound and the hydro salt 5,6-dimethoxy-2-methylbenzotellurazole.

EXAMPLE 54

3-Benzyl-2,5,6,-trimethylbenzotellurazolium Iodide,

R = CH$_2$— 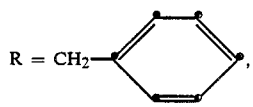,

R$^1$ = R$^2$—CH$_3$, X = I

C$_{17}$H$_{18}$INTe    mw = 490.84

This compound was prepared in the same way and on the same scale as the compound of Example 52, except that 2,5,6-trimethylbenzotellurazole (Example 22) was used in place of 2-methylbenzotellurazole and the product which was isolated directly from the reaction mixture was primarily the hydro salt of 2,5,6-tri-methylbenzotellurazole. The solvents were removed from the filtrate under reduced pressure. The residue was redissolved in acetone and treated with a saturated solution of sodium iodide in acetone. The solid isolated was washed and dried as before. Yield 0.10 g, m.p. 203°–206° C. (dec). The infrared and nuclear magnetic resonance spectra were in agreement with that expected for the structural formula.

EXAMPLE 55

2-Methyl-3-[2-(2,2-dimethyl-1,3-dioxolan-4-yl)ethyl]-benzotellurazolium Iodide,

R = CH$_2$CH$_2$— 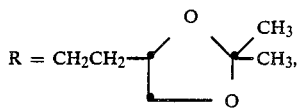,

R$^1$ = R$^2$ = H, X = I

C$_{15}$H$_{20}$INO$_2$Te    mw = 500.84

2-(2,2-Dimethyl-1,3-dioxolan-4-yl)ethyl trifluoromethane sulfonate was prepared in carbon tetrachloride solution and used as a dried solution in this example in the same way as 2-propen-1-yl trifluoromethanesulfonate was prepared and used in Examples 41 through 44, starting with 2,2-dimethyl-4-(2-hydroxyethyl)1,3-dioxolane and trifluoromethanesulfonate. 2-Methylbenzotellurazole (Example 18) (0.81 g, 0.0033 mole) was dissolved in dichloromethane (20 ml), and a solution of 2-(2,2-dimethyl-1,3-dioxolan-4-yl)ethyl trifluoromethanesulfonate in carbon tetrachloride was added from a dropping funnel at room temperature under a nitrogen atmosphere. After the addition was complete, the mixture was stirred for 21 hours at room temperature while maintaining a nitrogen atmosphere. The reaction mixture was filtered, and the solvent was removed from the filtrate under reduced pressure. The residue was dissolved in a small amount of acetone, and the solution was then treated with a saturated solution of sodium iodide in acetone. Diethyl ether was added to precipitate the product, which was isolated by filtration, washed with diethyl ether, and dried at room temperature under vacuum. The yield of pale yellow powder was 0.67 g (41% of theory), m.p. 158°–160° C. C, H and N elemental analyses and the infrared, nuclear magnetic resonance, and mass spectra of this sample were in agreement with that expected for the structural formula.

EXAMPLES 56–58

The following three compounds, Examples 56 through 58, were prepared by the same general procedure. The appropriate 2-methylbenzotellurazole base, 2-methylbenzotellurazole for Example 56, 5,6-dimethoxy-2-methylbenzotellurazole for Example 57, and 5-methoxy-2-methylbenzotellurazole for Example 58, was heated with trimethylene sulfate in equimolar amounts at 75° to 80° C. in a flask equipped with a magnetic stirrer and reflux condenser for 18 hours (3 hours in Example 58). The reactants initially formed a melt, but ultimately the mass became solid. After cooling to room temperature the solid was removed and then crushed and stirred in acetone until a uniform slurry was obtained. The solid was isolated by filtration, washed with more acetone and dried at room temperature under a vacuum. At least one product, Example 58, was observed to decompose on standing in air. Infrared, nuclear magnetic resonance, and mass spectra of each of these three examples were in agreement with that expected for the structural formulae.

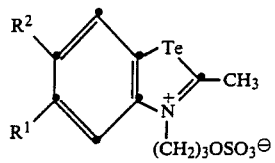

EXAMPLE 56

Anhydro-2-methyl-3-(3-sulfatopropyl)benzotellurazolium Hydroxide, $R^1=R^2=H$ $C_{11}H_{13}NO_4STe$    mw=382.88
Yield 79%, tan powder, m.p. 202°–204° C. (dec.).

EXAMPLE 57

Anhydro-5,6-dimethoxy-2-methyl-3-(3-sulfatopropyl)-benzotellurazolium Hydroxide, $R^1=R^2=OCH_3$ $C_{13}H_{17}NO_6STe$    mw=442.93
Yield 61%, tan powder, m.p. >250° C.

EXAMPLE 58

Anhydro-5-methoxy-2-methyl-3-(3-sulfatopropyl)benzothiazolium Hydroxide, $R^1=OCH_3$, $R^2=H$ $C_{12}H_{15}NO_5STe$    mw=412.91
Yield 79%, tan powder

EXAMPLES 59–61

Examples 59 through 61 illustrate the preparation of the 3-substituted naphtho[1,2-d]tellurazolium salts:

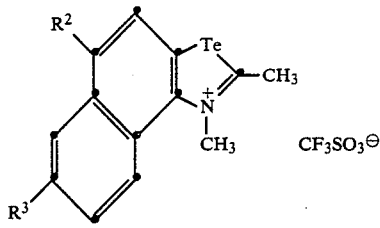

EXAMPLE 59

1,2-Dimethylnaphtho[1,2-d]tellurazolium Trifluoromethanesulfonate, $R^3=R^2=H$ $C_{14}H_{12}F_3NO_3STe$    mw=458.92

2-Methylnaphtho[1,2-d]tellurazole (Example 25) (14.8 g=0.05 mole) was dissolved in dry dichloromethane, and methyl trifluoromethanesulfonate (5.52 ml=0.05 mole) was added. The flask was sealed and kept over a weekend. Pale yellow plates (16.1 g, 70% of theory) formed. The product was recrystallized from 150 ml of acetone by addition of diethyl ether (m.p. 178°–183° C.). The mass and nuclear magnetic resonance spectra were in agreement with that expected for the structural formula.

EXAMPLE 60

7-Methoxy-1,2-dimethylnaphtho[1,2-d]tellurazolium Trifluoromethanesulfonate, $R^3=OCH_3$, $R^2=H$ $C_{15}H_{14}F_3NO_4STe$
    mw=488.93

7-Methoxy-2-methylnaphtho[1,2-d]tellurazole (Example 26) (0.98 g=0.03 mole) was alkylated as described above for Example 60. The reaction mixture was kept at room temperature for 5 days to yield 0.68 g, 46% of theory, yellow fluffy needles (m.p. 174°–183° C.). The mass and nuclear magnetic resonance spectra were in agreement with that expected for the structural formula.

EXAMPLE 61

1,2,5-Trimethylnaphtho[1,2-d]tellurazolium Trifluoromethanesulfonate, $R^3=H$, $R^2=CH_3$ $C_{15}H_{14}F_3NO_3STe$    mw=472.93

2,5-Dimethylnaphtho[1,2-d]tellurazole (Example 27) (0.93 g=0.003 mole) was dissolved in dry dichloromethane, and methyl trifluoromethanesulfonate (0.33 ml=0.003 mole) was added. The flask was sealed and kept over a weekend. Bright yellow plates (0.88 g, 61% of theory) formed. The product was recrystallized from 10 ml of acetone by addition of 20 ml of diethyl ether. The melting point was 224°–230° C. The mass and nuclear magnetic resonance spectra were in agreement with that expected for the structural formula.

EXAMPLES 62 THROUGH 64

The following three examples illustrate the preparation of 1-phenylisotellurazolo[1,5-a]benzotellurazoles of the following structure:

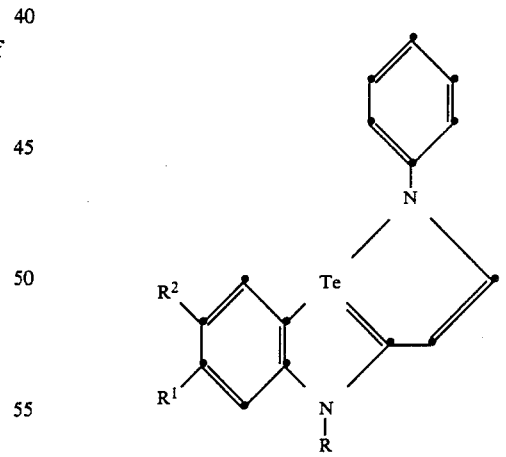

EXAMPLE 62

4-Methyl-1-phenylisotellurazolo[5,1-a]benzotellurazole, $R=CH_3$, $R_1=R^2=H$ $C_{16}H_{14}N_2Te$    mw=361.90

2,3-Dimethylbenzotellurazolium trifluoromethanesulfonate (0.82 g, 0.0002moles and N,N'-diphenylformamidine (0.80 g, 0.004 moles) were both dissolved in acetonitrile (25 ml). The solution was heated at reflux for 30 minutes. After chilling, the bright yellow solid which precipitated was filtered off and dried. Yield 0.20 g which was 28% of theory. The compound was recrystallized from methanol (175 ml). m.p. 180°–182° C. C, H, N and Te elemental analysis and both the mass spectrum and nuclear magnetic resonance spectra were consistent with the structure assigned.

EXAMPLE 63

6,7-Dimethoxy-4-methyl-1-phenylisotellurazolo[5,1-a]benzotellurazole, $R=CH_3$, $R_1=R^2=CH_3O$ $C_{18}H_{18}N_2O_2Te$    mw=421.96

5,6-Dimethoxy-2,3-dimethylbenzotellurazolium trifluoromethanesulfonate (1.00 g, 0.0021 moles) and N,N'-diphenylformamidine (0.80 g, 0.004 moles) were both dissolved in acetonitrile (50 ml). The solution was heated at reflux for 75 minutes and then chilled for three days. The solid was filtered off and dried. Yield 0.49 g, which was 43% of theory. It was recrystallized from ethanol (150 ml). The yield was 0.30 g which was 36% of theory of bright yellow needles. m.p. 186°–188° C. C, H, N and Te elemental analysis and both the mass spectrum and nuclear magnetic resonance spectrum were consistent with the structure assigned.

EXAMPLE 64

4,6,7-Trimethyl-1-phenylisotellurazolo[5,1-a]benzotellurazole, $R=R_1=R^2=CH_3$ $C_{18}H_{18}N_2Te$    mw=389.96

2,3,5,6-Tetramethylbenzotellurazolium trifluoromethanesulfonate (2.20 g, 0.005 moles) and N,N'-diphenylformamidine (0.98 g, 0.005 moles) were suspended in acetonitrile (15 ml) and heated at reflux for five minutes. Water was added until the reaction mixture became turbid. The product crystallized as yellow prisms. It was filtered off and dried. The yield was 0.75 g which was 38% of theory. The product was recrystallized from isopropanol (75 ml) m.p. 175°–177° C. C, H, N, and Te elemental analysis and both the mass spectrum and nuclear magnetic resonance spectrum were consistent with the structure assigned. Single crystal x-ray structural analysis confirmed the assigned structure.

The following exemplary compounds can also be produced employing preparation procedures analogous to those discussed above:

1. 4,6-Dimethyl-1-phenylisotellurazolo[1,5-a]benzotellurazole.
2. 6-Methoxy-4-methyl-1phenylisotellurazolo[1,5-a]benzotellurazole.
3. 4-Methyl-6-methylthio-1-phenylisotellurazolo[1,5-a]benzotellurazole.
4. 6-Hydroxy-4-methyl-1-phenylisotellurazolo[1,5-a]benzotellurazole.
5. 4-Methyl-6,7-methylenedioxy-1-phenylisotellurazolo[1,5-a]benzotellurazole.
6. 4-Ethyl-6-methyl-1-phenylisotellurazolo[1,5-a]benzotellurazole.
7. 4-Ethyl-6,7-dimethyl-1-phenylisotellurazolo[1,5-a]benzotellurazole.
8. 4-Ethyl-6-methoxy-1-phenylisotellurazolo[1,5-a]benzotellurazole.
9. 4-Ethyl-6,7-dimethoxy-1-phenylisotellurazolo[1,5-a]benzotellurazole.
10. 4-Benzyl-6,7-dimethoxy-1-phenylisotellurazolo[1,5-a]benzotellurazole.
11. 4-Ethoxycarbonylmethyl-6-methoxy-1-phenylisotellurazolo[1,5-a]benzotellurazole.
12. 6,7-Dimethyl-1-phenyl-4-(2-propen-1-yl)isotellurazolo[1,5-a]benzotellurazole.
13. 6,7-Dimethoxy-1-phenyl-4-(3-sulfatopropyl)isotellurazolo[1,5-a]benzotellurazole.
14. 4-Ethyl-6-phenoxy-1-phenylisotellurazolo[1,5-a]benzotellurazole.
15. 4-Cyclopropyl-6,7-dimethoxy-1-phenylisotellurazolo[1,5-a]benzotellurazole.
16. 6-Hydroxymethyl-4-methyl-1-phenylisotellurazolo[1,5-a]benzotellurazole.
17. 4-Ethyl-1-phenyl-6-phenylthioisotellurazolo[1,5-a]benzotellurazole.
18. 11-Methyl-8-phenylisotellurazolo[5,1-b]naphtho[1,2-d]tellurazole.
19. 3-Methoxy-11-methyl-8-phenylisotellurazolo[5,1-b]naphtho[1,2-d]tellurazole.
20. 5,11-Dimethyl-8-phenylisotellurazolo[5,1-b]naphtho[1,2-d]tellurazole.

All of these compounds by reason of sharing the heterocyclic ring structure are stable and are capable of absorbing blue light.

From the foregoing discussion it is apparent that the compounds of this invention can take a variety of forms and share similar characteristics. This invention has been described in detail with reference to preferred embodiments thereof, but it will be understood that variations and modifications can be effected within the spirit and scope of the invention.

What is claimed is:

1. A heterocycle represented by the formula:

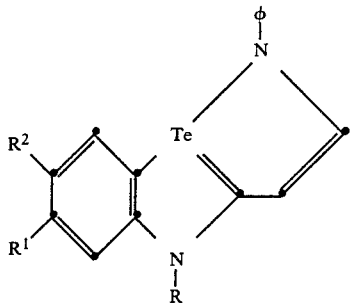

wherein

R is comprised of
a hydrocarbon group selected from among alkyl of from 1 to 6 carbon atoms, cycloalkyl of from 3 to 8 carbon atoms, alkenyl of from 2 to 6 carbon atoms, alkynyl of from 2 to 6 carbon atoms, aryl of from 6 to 10 carbon atoms, and aralkyl or alkaryl the alkyl moiety of which contains from 1 to 6 carbon atoms and the aryl moiety of which contains from 6 to 10 carbon atoms, said hydrocarbon group being unsubstituted or halo substituted where halo is chosen from the class consisting of fluoro, chloro, bromo, and iodo substituents, oxyalkyl, oxyaryl, oxyalkaryl, oxyalkaryl, thioalky, thioaryl, thioalkaryl, or thioaralkyl substituted wherein the alkyl moieties in each instance contain from 1 to 6 carbon atoms and the aryl moieties contain 6 to 10 carbon atoms, or —S(O-

$_2$)OM' or —OS(O$_2$)OM' substituted, where M' is hydrogen, ammonium, an alkali metal, alkyl of from 1 to 6 carbon atoms, or aryl of from 6 to 10 carbon atoms, R$^1$ and R$^2$ are individually chosen from among hydrogen, hydroxy, hydroxyalkyl, alkyl, alkoxy, alkylthio, aryloxy, arylthio, hydroxyaryl, and —N(R$^4$)$_2$, where the alkyl moieties contain from 1 to 6 carbon atoms, the aryl moieties contain from 6 to 10 carbon atoms, and R$^4$ is independently in each occurrence hydrogen or R; or R$^1$ and R$^2$ together form a —O—(CH$_2$)$_n$—O— linkage, where n is preferably 1 to 3; and φ is an unsubstituted phenyl group or an R substituted phenyl group.

2. A heterocycle according to claim 1 wherein no one of the substituents R, R$^1$, and R$^2$ account for more than 10 carbon atoms.

3. A heterocycle represented by the formula:

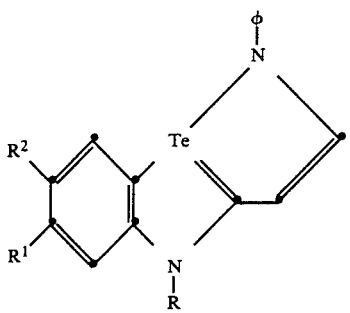

wherein

R is chosen from the class consisting of alkyl, benzyl, alkenyl of from 2 to 6 carbon atoms, sulfoalkyl, and sulfatoalkyl, wherein each alkyl moiety contains from 1 to 6 carbon atoms;

R$^1$ and R$^2$ are chosen independently from the class consisting of hydrogen, alkyl, alkoxy, alkylthio, and phenoxy wherein each alkyl moiety contains from 1 to 6 carbon atoms or together form a —O—(CH$_2$)$_n$—O— linkage, where n is preferably 1 to 3; and φ is phenyl.

4. A heterocycle according to claim 3 wherein each alkyl moiety contains from 1 to 3 carbon atoms.

5. A process of preparing a 1-phenylisotellurazolo[1,5-a]benzotellurazole of the formula

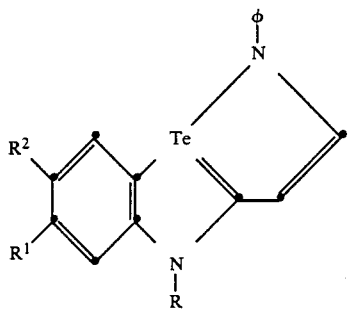

by preparing a 2-methylbenzotellurazole heterocycle of the formula:

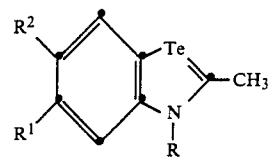

with

φ—NH—CH=N—φ' wherein

R is comprised of a hydrocarbon group selected from among alkyl of from 1 to 6 carbon atoms, cycloalkyl of from 3 to 8 carbon atoms, alkenyl of from 2 to 6 carbon atoms, alkynyl of from 2 to 6 carbon atoms, aryl of from 6 to 10 carbon atoms, and aralkyl or alkaryl the alkyl moiety of which contains from 1 to 6 carbon atoms and the aryl moiety of which contains from 6 to 10 carbon atoms, said hydrocarbon group being unsubstituted or halo substituted where halo is chosen from the class consisting of fluoro, chloro, bromo, and iodo substituents, oxyalkyl, oxyaryl, oxyalkaryl, oxyalkaryl, thioalky, thioaryl, thioalkaryl, or thioaralkyl substituted wherein the alkyl moieties in each instance contain from 1 to 6 carbon atoms and the aryl moieties contain 6 to 10 carbon atoms, or —S(O$_2$)OM' or —OS(O$_2$)OM' substituted, where M' is hydrogen, ammonium, an alkali metal, alkyl of from 1 to 6 carbon atoms, or aryl of from 6 to 10 carbon atoms, R$^1$ and R$^2$ are individually chosen from among hydrogen, hydroxy, hydroxyalkyl, alkyl, alkoxy, alkylthio, aryloxy, arylthio, hydroxyaryl, and —N(R$^4$)$_2$, where the alkyl moieties contain from 1 to 6 carbon atoms, the aryl moieties contain from 6 to 10 carbon atoms, and R$^4$ is independently in each occurrence hydrogen or R; or R$^1$ and R$^2$ together form a —O—(CH$_2$)$_n$—O— linkage, where n is preferably 1 to 3; and φ and φ' are each an unsubstituted phenyl group or an R substituted phenyl group.

6. A porcess of preparing a 1-phenylisotellurazolo[1,5-a]benzotellurazole of the formula

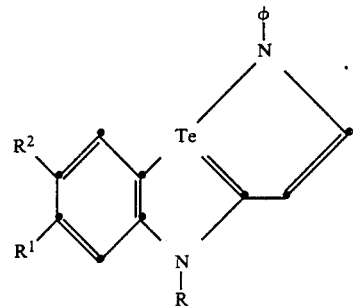

by preparing a 2-methylbenzotellurazole heterocycle of the formula:

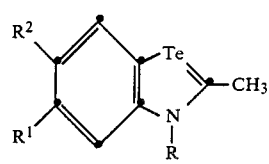

with

φ—NH—CH=Nφ' wherein

R is chosen from the class consisting of alkyl benzyl, alkenyl of from 2 to 6 carbon atoms, sulfoalkyl, and sulfatoalkyl, wherein each alkyl moiety contains from 1 to 6 carbon atoms;

$R^1$ and $R^2$ are chosen independently from the class consisting of hydrogen, alkyl, alkoxy, alkylthio, and phenoxy wherein each alkyl moiety contains from 1 to 6 carbon atoms or together form a —O—$(CH_2)_n$—O— linkage, where n is preferably 1 to 3; and φ is phenyl.

7. A heterocycle represented by the formula:

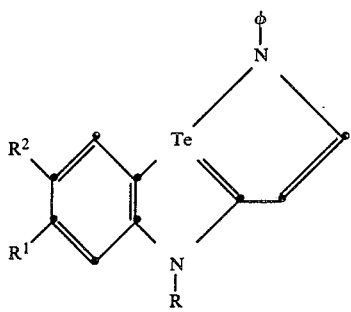

wherein

R is comprised of
a hydrocarbon group selected from among alkyl of from 1 to 6 carbon atoms, cycloalkyl of from 3 to 8 carbon atoms, alkenyl of from 2 to 6 carbon atoms, alkynyl of from 2 to 6 carbon atoms, aryl of from 6 to 10 carbon atoms, and aralkyl or alkaryl the alkyl moiety of which contains from 1 to 6 carbon atoms and the aryl moiety of which contains from 6 to 10 carbon atoms,
said hydrocarbon group being substituted with a carboxylate-forming substituent having from 1 to 8 carbon atoms;

$R^1$ and $R^2$ are individually chosen from among hydrogen, hydroxy, hydroxyalkyl, alkyl, alkoxy, alkylthio, aryloxy, arylthio, hydroxyaryl, and —$N(R^4)_2$, where the alkyl moieties contain from 1 to 6 carbon atoms, the aryl moieties contain from 6 to 10 carbon atoms, and $R^4$ is independently in each occurrence hydrogen or R; or $R^1$ and $R^2$ together form a —O—$(CH_2)_n$—O— linkage, where n is preferably 1 to 3; and φ is an unsubstituted phenyl group or an R substituted phenyl group.

8. A process of preparing a 1-phenylisotellurazolo[1,5-a]benzotellurazole of the formula

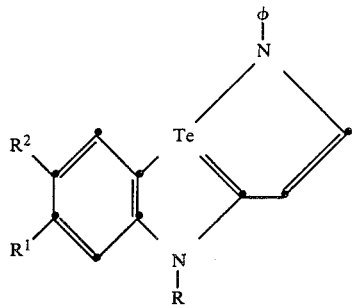

by preparing a 2-methylbenzotellurazole heterocycle of the formula:

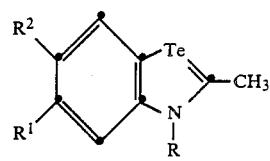

with

φ—NH—CH=N—φ' wherein

R is comprised of
a hydrocarbon group selected from among alkyl of from 1 to 6 carbon atoms, cycloalkyl of from 3 to 8 carbon atoms, alkenyl of from 2 to 6 carbon atoms, alkynyl of from 2 to 6 carbon atoms, aryl of from 6 to 10 carbon atoms, and aralkyl or alkaryl the alkyl moiety of which contains from 1 to 6 carbon atoms and the aryl moiety of which contains from 6 to 10 carbon atoms,
said hydrocarbon group being substituted with a carboxylate-forming substituent having from 1 to 8 carbon atoms;

$R^1$ and $R^2$ are individually chosen from among hydrogen, hydroxy, hydroxyalkyl, alkyl, alkoxy, alkylthio, aryloxy, arylthio, hydroxyaryl, and —$N(R^4)_2$, where the alkyl moieties contain from 1 to 6 carbon atoms, the aryl moieties contain from 6 to 10 carbon atoms, and $R^4$ is independently in each occurrence hydrogen or R; or $R^1$ and $R^2$ together form a —O—$(CH_2)_n$—O— linkage, where n is preferably 1 to 3; and φ and φ' are each an unsubstituted phenyl group or an R substituted phenyl group.

9. A 1-arylisotellurazolo[1,5-a] aromatic tellurazole chosen from the class consisting of
4-methyl-1-phenylisotellurazolo[5,1-a]benzotellurazole,
6,7-dimethoxy-4-methyl-1-phenylisotellurazolo[5,1-a]benzotellurazole,
4,6,7-trimethyl-1-phenylisotellurazolo[5,1-a]benzotellurazole,
4,6-dimethyl-1-phenylisotellurazolo[1,5-a]benzotellurazole,
6-methoxy-4-methyl-1-phenylisotellurazolo[1,5-a]benzotellurazole,
4-methyl-6-methylthio-1-phenylisotellurazolo[1,5-a]benzotellurazole,
6-hydroxy-4-methyl-1-phenylisotellurazolo[1,5-a]benzotellurazole, 4-methyl-6,7-methylenedioxy-1-phenylisotellurazolo[1,5-a]benzotellurazole,
4-ethyl-6-methyl-1-phenylisotellurazolo[1,5-a]benzotellurazole,
4-ethyl-6,7-dimethyl-1-phenylisotellurazolo[1,5-a]benzotellurazole,
4-ethyl-6-methoxy-1-phenylisotellurazolo[1,5-a]benzotellurazole,
4-ethyl-6,7-dimethoxy-1-phenylisotellurazolo[1,5-a]benzotellurazole,
4-benzyl-6,7-dimethoxy-1-phenylisotellurazolo[1,5-a]benzotellurazole,
4-ethoxycarbonylmethyl-6-methoxy-1-phenylisotellurazolo[1,5-a]benzotellurazole,
6,7-dimethyl-1-phenyl-4-(2-propen-1yl)isotellurazolo[1,5-a]benzotellurazole,
6,7-dimethoxy-1-phenyl-4-(3-sulfatopropyl)isotellurazolo[1,5-a]benzotellurazole,
4-ethyl-6-phenoxy-1-phenylisotellurazolo[1,5-a]benzotellurazole,
4-cyclopropyl-6,7-dimethoxy-1-phenylisotellurazolo[1,5-a]benzotellurazole,
6-hydroxymethyl-4-methyl-1-phenylisotellurazolo[1,5-a]benzotellurazole,
4-ethyl-1-phenyl-6-phenylthioisotellurazolo]1,5-a]benzotellurazole,
11-methyl-8-phenylisotellurazolo[5,1-b]naphtho[1,2-d]tellurazole,
3-methoxy-11-methyl-8-phenylisotellurazolo[5,1-b]naphtho[1,2-d]tellurazole, and
5,11-dimethyl-8-phenylisotellurazolo[5,1-b]naphtho[1,2-d]tellurazole.

* * * * *